(12) United States Patent
Roelvink et al.

(10) Patent No.: US 8,008,468 B2
(45) Date of Patent: *Aug. 30, 2011

(54) RNAI EXPRESSION CONSTRUCTS WITH LIVER-SPECIFIC ENHANCER/PROMOTER

(75) Inventors: Petrus W. Roelvink, Campbell, CA (US); David A. Suhy, Castro, CA (US); Alexander A. Kolykhalov, Mountain View, CA (US); Mark A. Kay, Los Altos, CA (US); Jeffery C. Giering, Burlingame, CA (US)

(73) Assignee: Benitec, Inc., Melbourne (AU)

( * ) Notice: Subject to any disclaimer, the term of this patent is extended or adjusted under 35 U.S.C. 154(b) by 188 days.

This patent is subject to a terminal disclaimer.

(21) Appl. No.: 11/355,516

(22) Filed: Feb. 16, 2006

(65) Prior Publication Data

US 2006/0189561 A1 Aug. 24, 2006

Related U.S. Application Data

(60) Provisional application No. 60/653,616, filed on Feb. 16, 2005.

(51) Int. Cl.
C07H 21/04 (2006.01)
(52) U.S. Cl. ............... 536/24.5; 536/24.31; 536/24.1; 514/44
(58) Field of Classification Search .................. None
See application file for complete search history.

(56) References Cited

U.S. PATENT DOCUMENTS

| | | | |
|---|---|---|---|
| 6,218,181 B1 | 4/2001 | Verma et al. | |
| 6,509,323 B1 | 1/2003 | Davis et al. | |
| 6,573,099 B2 | 6/2003 | Graham | |
| 6,808,905 B2 | 10/2004 | McArthur et al. | |
| 2004/0214329 A1 | 10/2004 | Kay et al. | |
| 2004/0220130 A1* | 11/2004 | Robbins et al. | 514/44 |
| 2005/0008617 A1* | 1/2005 | Chen et al. | 424/93.2 |

OTHER PUBLICATIONS

Anderson et al. Bispecific Short Hairpin siRNA constructs targeted to CD4, CXCR$ and CCR5 Confer HIV-1 Resistance. Oligonucleotides 2003, vol. 13, pp. 303-312.*
Wu et al. Inhibition of hepatitis viral replication by siRNA. Expert Opinion Biol. Ther. 2004, vol. 4(10), pp. 1649-1659.*
Wilson et al. RNA interference blocks gene expression and RNA synthesis from hepatitis C replicons propagated in human liver cells. PNAS 2003, vol. 100m No. 5, pp. 2783-2788.*
Maniatis et al., *Molecular Cloning: A Laboratory Manual*, Cold Spring Harbor Press, Cold Spring Harbor, NY (1982).
Sambrook et al.,*Molecular Cloning: A Laboratory Manual*, 2nd Ed., Cold Spring Harbor Press, Cold Spring Harbor, NY (1989).
D.N. Glover, *DNA Cloning: A Practical Approach*, vols. I and II, Oxford University Press (1985).
M.J. Gait, *Oligonucleotide Synthesis: A Practical Approach*, Oxford University Press (1984).
B.D. Hames et al, *Nucleic Acid Hybridization: A Practical Approach*, Oxford University Press (1984).
R.I. Freshney *Animal Cell Culture*, IRL Press (1986).
J.A. Cann et al., *RNA Viruses: A Practical Approach*, Oxford University Press (2000).
McOmie, *Protective Groups in Organic Chemistry*, ed., Plenum Press, NY, NY (1973).
Greene, Protective *Groups in Organic Synthesis*, ed., John Wiley & Sons, NY (1981).
Karlin, S. et al., "Applications and Statistics for Multiple High-Scoring Segments in Molecular Sequences", *Proc. Natl. Acad. Sci.*, 1993, vol. 90, No. 12, pp. 5873-5877.
Pearson et al., "Improved Tools for Biological Sequence Comparison," *Proceedings of the National Academy of Science of the United States of America*, 1988, vol. 85, pp. 2444-2448.
Myers et al., Optimal Alignments in Linear Space, *CABIOS*, 1988, vol. 4, No. 1, pp. 11-17.
Fire et al., "Potent and Specific Genetic Interference by Double-Stranded RNA in Caenorhabditis elegans," *Nature*, 1998, vol. 391, pp. 806-811.
Tuschl et al., "Targeted mRNA Degradation by Double-Stranded RNA in Vitro" *Genes & Development*, 1999, vol. 13, pp. 3191-3197.
Elbashir et al., "Duplexes of 21-Nucleotide RNAs Mediate RNA Interference in Cultured Mammalian Cells," *Nature*, 2001, vol. 411, pp. 494-498.
Kurreck, J., "Antisense Technologies: Improvement Through Novel Chemical Modifications," *Eur. J. Biochem*, 2003, vol. 270, pp. 1628-1644.
Harborth et al., "Sequence, Chemical, and Structural Variation of Small Interfering RNAs and Short Hairpin RNAs and the Effect of Mammalian Gene Silencing," *Antisense and Nucleic Acid Drug Development*, 2003, vol. 13, pp. 83-105.
Ashfield et al., "MAZ-Dependent Termination Between Closely Spaced Human Complement Genes," *The EMBO Journal*, 1994, vol. 13, No. 23, pp. 5656-5667.
Yonaha et al., "Transcriptional Termination and Coupled Polyadenylation in Vitro," *The EMBO Journal*, 2000, vol. 19, No. 14, pp. 3770-3777.
Gitlin et al., "Poliovirus Escape from RNA Interference: Short Interfering RNA-Target Recognition and Implications for Therapeutic Approaches," *Journal of Virology*, 2005, vol. 79, No. 2, pp. 1027-1035.
Nakai et al., "A Limited Number of Transducible Hepatocytes Restricts a Wide-Range Linear Vector Dose Response in Recombinant Adeno-Associated Virus-Mediated Liver Transduction," *Journal of Virology*, 2002, vol. 76, No. 22, pp. 11343-11349.
Kay et al., "Looking into the Safety of AAV Vectors," *Nature*, vol. 424, p. 251, 2003.
Thomas et al., "Progress and Problems with the Use of Viral Vectors for Gene Therapy," *Nature Reviews, Genetics*, 2003, vol. 4, pp. 346-358. Tomar et al., "Use of Adeno-Associated Viral Vector for Delivery of Small Interfering RNA," *Oncogene*, 2003, vol. 22, pp. 5712-5715.
Boden et al., "Human Immunodeficiency Virus Type 1 Escape from RNA Interference," *Journal of Virology*, 2003, vol. 77, No. 21, 11531-11535.
Mingozzi et al., "Improved Hepatic Gene Transfer by Using an Adeno-Associated Virus Serotype 5 Vector," *Journal of Virology*, 2002, vol. 76, No. 20, pp. 10497-10502.

(Continued)

Primary Examiner — Kimberly Chong
(74) Attorney, Agent, or Firm — Patton Boggs LLP

(57) ABSTRACT

The present invention provides compositions and methods suitable for RNAi specifically in the liver so as to treat diseases or disorders.

16 Claims, 19 Drawing Sheets

OTHER PUBLICATIONS

Thomas et al., "Rapid Uncoating of Vector Genomes is the Key to Efficient Liver Transduction with Pseudotyped Adeno-Associated Virus Vectors," *Journal of Virology*, 2004, vol. 78, No. 6, pp. 3110-3122.

Grimm et al., "Preclinical in Vivo Evaluation of Pseudotyped Adeno-Associated Virus Vectors for Liver Gene Therapy," *Blood*, 2003, vol. 102, No. 7, pp. 2412-2419.

Wang et al., "Rapid and Highly Efficient Transduction by Double-Stranded Adeno-Associated Virus Vectors in Vitro and in Vivo," *Gene Therapy*, 2003, vol. 10, pp. 2105-2111.

Nakai et al., "Unrestricted Hepatocyte Transduction with Adeno-Associated Virus Serotype 8 Vectors in Mice," *Journal of Virology*, 2005, vol. 79, No. 1, pp. 214-224.

Grimm et al., "Liver Transduction with Recombinant Adeno-Associated Virus is Primarily Restricted by Capsid Serotype Not Vector Genotype," *Journal of Virology*, 2006, vol. 80, No. 1, pp. 426-439.

Yant et al., "Transposition from a Gutless Adeno-Transposon Vector Stabilizes Transgene Expression in Vivo," *Nature: Biotechnology*, 2002, vol. 20, pp. 999-1005.

Perri et al., "Replicon Vectors Derived from Sindbis Virus and Semliki Forest Virus that Establish Persistent Replication in Host Cells," *Journal of Virology*, 2000, vol. 74, No. 20, pp. 9802-9807.

Chen et al., "Minicircle DNA Vectors Devoid of Bacterial DNA Result in Persistent and High-Level Transgene Expression in Vivo," *Molecular Therapy*, 2003, vol. 8, No. 3, pp. 495-500.

Tang et al., "Genetic Immunization is a Simple Method for Eliciting an Immune Response," *Nature*, 1992, vol. 356, pp. 152-154.

Yokota et al., "Inhibition of Intracellular Hepatitis C Virus Replication by Synthetic and Vector-Derived Small Interfering RNAs," *EMBO Reports*, 2003, vol. 4, No. 6, pp. 602-608.

Miao et al., "Inclusion of the Hepatic Locus Control Region, an Intron, and Untranslated Region Increases and Stabilizes Hepatic Factor IX Gene Expression in Vivo but NOT in Vitro," *Molecular Therapy*, 2000, vol. 1, No. 6, pp. 522-532.

\* cited by examiner

FIG. 8A   48 hours

FIG. 8B      72 hours

FIG. 9A
Apo E enhancer agatctGCTGTTTGTGTGCTGCCTCTGAAGTCCACACTGAACAAACTTCAGCCTACTCATGTCCCTAAAAT
GGGCAAACATTGCAAGCAGCAAACAGCAAACACACAGCCCTCCCTGCCTGCTGACCTTGGAGCTGGGGCAG
AGGTCAGAGACCTCTCTGagatct Note: The enhancer sequence shown here is part of a larger regulatory region called the ApoE enhancer region. However, literature studies have shown that this is the core functional element necessary for activity. Element shown here is flanked by two BglII sites that do not naturally occur in the sequence itself.

FIG. 9B
Synthetic Enhancer Sequence

Agatctgtcaattcacgcgagttaataattaccagcgcgggccaaataaataatccgcgaggggcaggtgacgtttgcccagc
gcgcgctggtaattattaacctcgcgaatattgattcgaggccgcgattgccgcaatcgcgaggggcaggtgacctttgcccag
cgcgcgttcgccccgccccggacggtatcgatgtcgaggggatcccactgggaggatgttgagtaagatggaaaactactga
tgaccttgcagagacagagtattaggacatgtttgaacaggggccgggcgatcagcaggtagctctagaggtaccccagatct Note: As shown here, this sequence starts and ends with the cloning site BglII

FIG. 9C
hAAT promoter agatctttgctaccagtggaacagccactaaggattctgcagtgagagcagagggccagctaagtggtact
ctcccagagactgtctgactcacgccaccccctccaccttggacacaggacgctgtggtttctgagccagg
tacaatgactccttcggtaagtgcagtggaagctgtacactgcccaggcaaagcgtccgggcagcgtagg
cgggcgactcagatcccagccagtggacttagcccctgtttgctcctccgataactggggtgaccttggtt
aatattcaccagcagcctcccccgttgcccctct GGTACCACTGCTTAAATACGGACGAGGACAGGGC <u>CAG</u>

Note: The sequence shown here represents the hAAT promoter sequence. The promoter starts with a BglII cloning site and ends with the first 3 nucleotides of the blunt enzyme PvuII. A KpnI site is shown in bold face print. Normally this is a BamHI site. This would have interfered with our cloning strategy and was therefore changed to KpnI. This change does not affect activity of the promoter.

FIG. 9D
LCAT promoter sequence agatctctgggcctcaaaatggagatggatcccaggtcttgtgggaccctgggatgtttggggactttact
atctagcaccccagtaggcctgtcctggccagagaagactggtaggggccgagtggggtttgaaggcagcc
ggcccggcccagcccaggagcgctatttattgcatatttattgtttggatgtcaccatcagagacgaaggg
aagggtagccagggagggagtccagcccagctgcctgcaggagaatctggctcagtctactatgggcaggg
ccccccaccaagctgagccgaatggagacagctgagctgaggcctgacttttttcaataaaacattgtgtag
ttctgggcctcctgctgccccggctctgtttcccctggcgccaagagaagaaggcggaactgaacccaggc
ccagagccggctccctgaggctgtgcccctttccggcaatctctggccacaaccccactggccaggccgt
ccctcccactggccctagggcccctcccactcccacaccagataaggacagcccagtgccgtc Note promoter starts with a BglII cloning site and ends with the first 3 nucleotides of the blunt enzyme HincII.

FIG. 9E

ApoH promoter sequence agatctgagagtaggtgtttgtccaaagtttatatgccaaggctgtgagtgaaacaggagcttcgatcttt
tggtgttccatctacaacatacacaaaacaaaagatggagaatgagaagtccaggcaacccccggaaacaac
aagtttctgtcaaaagcaataatgaactgttttgtgccattaacaaaaacgttatgaagacagaaaccatc
tcccaaagatttcataacagagccacataagtggaaagtaaatgattaaagaatgtgggtctcagagttcc
attcaaatcatgatactttatcttctatttacaaagataaaagtacaccagaaaatggttaatgtttaagc
gctttcatatttggctctgtcttttagcagacgaaaaccactttggCAG Note promoter starts with a BglII cloning site and ends with the first 3 nucleotides of the blunt enzyme PvuII.

FIG. 9F

The Transthyretin Promoter agatctagtgtctgtctgcacatttcgtagagcgagtgttccgatactctaatctccctaggcaaggttcatatttgtgtaggttactta
ttctccttttgttgactaagtcaataatcagaatcagcaggtttggagtcagcttggcagggatcagcagcctgggttggaaggag
ggggtataaaagccccttcaccaggagaagcccagctg Note: As shown here the sequence starts with the cloning site BglII and ends with PvuII.
Duplex DNA fragments coding for shRNA are ligated onto this site.

SEQUENCE LISTING

<160> NUMBER OF SEQ ID NOS: 64

<210> SEQ ID NO 1
<211> LENGTH: 20
<212> TYPE: DNA
<213> ORGANISM: Artificial
<220> FEATURE:
<223> OTHER INFORMATION: oligonucleotide

<400> SEQUENCE: 1
gctgtgagga actactgtct         20

<210> SEQ ID NO 2
<211> LENGTH: 19
<212> TYPE: DNA
<213> ORGANISM: Artificial
<220> FEATURE:

<223> OTHER INFORMATION: oligonucleotide

<400> SEQUENCE: 2
gtctagccat ggcgttagt                                                    19

<210> SEQ ID NO 3
<211> LENGTH: 19
<212> TYPE: DNA
<213> ORGANISM: Artificial
<220> FEATURE:
<223> OTHER INFORMATION: oligonucleotide

<400> SEQUENCE: 3
ggagagccat agtggtctg                                                    19

<210> SEQ ID NO 4
<211> LENGTH: 19
<212> TYPE: DNA
<213> ORGANISM: Artificial
<220> FEATURE:
<223> OTHER INFORMATION: oligonucleotide

<400> SEQUENCE: 4
gcggaaccgg tgagtacac                                                    19

<210> SEQ ID NO 5
<211> LENGTH: 20
<212> TYPE: DNA
<213> ORGANISM: Artificial
<220> FEATURE:
<223> OTHER INFORMATION: oligonucleotide

<400> SEQUENCE: 5
gtctgcggaa ccggtgagta                                                   20

<210> SEQ ID NO 6
<211> LENGTH: 20
<212> TYPE: DNA
<213> ORGANISM: Artificial
<220> FEATURE:
<223> OTHER INFORMATION: oligonucleotide

<400> SEQUENCE: 6
gcgaaaggcc ttgtggtact                                                   20

<210> SEQ ID NO 7
<211> LENGTH: 19
<212> TYPE: DNA
<213> ORGANISM: Artificial
<220> FEATURE:
<223> OTHER INFORMATION: oligonucleotide

<400> SEQUENCE: 7
gatagggtgc ttgcgagtg                                                    19

<210> SEQ ID NO 8
<211> LENGTH: 20
<212> TYPE: DNA
<213> ORGANISM: Artificial
<220> FEATURE:
<223> OTHER INFORMATION: oligonucleotide

<400> SEQUENCE: 8
gaggtctcgt agaccgtgca                                                   20

<210> SEQ ID NO 9

```
<211> LENGTH: 20
<212> TYPE: DNA
<213> ORGANISM: Artificial
<220> FEATURE:
<223> OTHER INFORMATION: oligonucleotide

<400> SEQUENCE: 9
gcttgtggta ctgcctgata                                               20

<210> SEQ ID NO 10
<211> LENGTH: 20
<212> TYPE: DNA
<213> ORGANISM: Artificial
<220> FEATURE:
<223> OTHER INFORMATION: oligonucleotide

<400> SEQUENCE: 10
gctgcctgat agggtgcttg                                               20

<210> SEQ ID NO 11
<211> LENGTH: 19
<212> TYPE: DNA
<213> ORGANISM: Artificial
<220> FEATURE:
<223> OTHER INFORMATION: oligonucleotide

<400> SEQUENCE: 11
atcactcccc tgtgaggaa                                                19

<210> SEQ ID NO 12
<211> LENGTH: 19
<212> TYPE: DNA
<213> ORGANISM: Artificial
<220> FEATURE:
<223> OTHER INFORMATION: oligonucleotide

<400> SEQUENCE: 12
actcccctgt gaggaacta                                                19

<210> SEQ ID NO 13
<211> LENGTH: 19
<212> TYPE: DNA
<213> ORGANISM: Artificial
<220> FEATURE:
<223> OTHER INFORMATION: oligonucleotide

<400> SEQUENCE: 13
cgtctagcca tggcgttag                                                19

<210> SEQ ID NO 14
<211> LENGTH: 19
<212> TYPE: DNA
<213> ORGANISM: Artificial
<220> FEATURE:
<223> OTHER INFORMATION: oligonucleotide

<400> SEQUENCE: 14
tctagccatg gcgttagta                                                19

<210> SEQ ID NO 15
<211> LENGTH: 19
<212> TYPE: DNA
<213> ORGANISM: Artificial
<220> FEATURE:
<223> OTHER INFORMATION: oligonucleotide

<400> SEQUENCE: 15
```

-continued ctagccatgg cgttagtat                                                19

<210> SEQ ID NO 16
<211> LENGTH: 19
<212> TYPE: DNA
<213> ORGANISM: Artificial
<220> FEATURE:
<223> OTHER INFORMATION: oligonucleotide

<400> SEQUENCE: 16
tgtcgtacag cctccaggc                                                19

<210> SEQ ID NO 17
<211> LENGTH: 19
<212> TYPE: DNA
<213> ORGANISM: Artificial
<220> FEATURE:
<223> OTHER INFORMATION: oligonucleotide

<400> SEQUENCE: 17
ccgggagagc catagtggt                                                19

<210> SEQ ID NO 18
<211> LENGTH: 19
<212> TYPE: DNA
<213> ORGANISM: Artificial
<220> FEATURE:
<223> OTHER INFORMATION: oligonucleotide

<400> SEQUENCE: 18
agagccatag tggtctgcg                                                19

<210> SEQ ID NO 19
<211> LENGTH: 19
<212> TYPE: DNA
<213> ORGANISM: Artificial
<220> FEATURE:
<223> OTHER INFORMATION: oligonucleotide

<400> SEQUENCE: 19
gccatagtgg tctgcggaa                                                19

<210> SEQ ID NO 20
<211> LENGTH: 19
<212> TYPE: DNA
<213> ORGANISM: Artificial
<220> FEATURE:
<223> OTHER INFORMATION: oligonucleotide

<400> SEQUENCE: 20
ccggtgagta caccggaat                                                19

<210> SEQ ID NO 21
<211> LENGTH: 19
<212> TYPE: DNA
<213> ORGANISM: Artificial
<220> FEATURE:
<223> OTHER INFORMATION: oligonucleotide

<400> SEQUENCE: 21
cggtgagtac accggaatc                                                19

<210> SEQ ID NO 22
<211> LENGTH: 19
<212> TYPE: DNA
<213> ORGANISM: Artificial
<220> FEATURE:

```
<223> OTHER INFORMATION: oligonucleotide

<400> SEQUENCE: 22
gactgggtcc tttcttgga                                            19

<210> SEQ ID NO 23
<211> LENGTH: 19
<212> TYPE: DNA
<213> ORGANISM: Artificial
<220> FEATURE:
<223> OTHER INFORMATION: oligonucleotide

<400> SEQUENCE: 23
gaccgggtcc tttcttgga                                            19

<210> SEQ ID NO 24
<211> LENGTH: 19
<212> TYPE: DNA
<213> ORGANISM: Artificial
<220> FEATURE:
<223> OTHER INFORMATION: oligonucleotide

<400> SEQUENCE: 24
accgggtcct ttcttggaa                                            19

<210> SEQ ID NO 25
<211> LENGTH: 19
<212> TYPE: DNA
<213> ORGANISM: Artificial
<220> FEATURE:
<223> OTHER INFORMATION: oligonucleotide

<400> SEQUENCE: 25
tgggttgcga aaggccttg                                            19

<210> SEQ ID NO 26
<211> LENGTH: 19
<212> TYPE: DNA
<213> ORGANISM: Artificial
<220> FEATURE:
<223> OTHER INFORMATION: oligonucleotide

<400> SEQUENCE: 26
ttgcgaaagg ccttgtggt                                            19

<210> SEQ ID NO 27
<211> LENGTH: 19
<212> TYPE: DNA
<213> ORGANISM: Artificial
<220> FEATURE:
<223> OTHER INFORMATION: oligonucleotide

<400> SEQUENCE: 27
aggccttgtg gtactgcct                                            19

<210> SEQ ID NO 28
<211> LENGTH: 19
<212> TYPE: DNA
<213> ORGANISM: Artificial
<220> FEATURE:
<223> OTHER INFORMATION: oligonucleotide

<400> SEQUENCE: 28
tagggtgctt gcgagtgcc                                            19

<210> SEQ ID NO 29
```

```
<211> LENGTH: 19
<212> TYPE: DNA
<213> ORGANISM: Artificial
<220> FEATURE:
<223> OTHER INFORMATION: oligonucleotide

<400> SEQUENCE: 29
cgggaggtct cgtagaccg                                              19

<210> SEQ ID NO 30
<211> LENGTH: 19
<212> TYPE: DNA
<213> ORGANISM: Artificial
<220> FEATURE:
<223> OTHER INFORMATION: oligonucleotide

<400> SEQUENCE: 30
ggtctcgtag accgtgcat                                              19

<210> SEQ ID NO 31
<211> LENGTH: 19
<212> TYPE: DNA
<213> ORGANISM: Artificial
<220> FEATURE:
<223> OTHER INFORMATION: oligonucleotide

<400> SEQUENCE: 31
agatcgttgg tggagttta                                              19

<210> SEQ ID NO 32
<211> LENGTH: 20
<212> TYPE: DNA
<213> ORGANISM: artificial
<220> FEATURE:
<223> OTHER INFORMATION: oligonucleotide

<400> SEQUENCE: 32
gttgggtaag gtcatcgata                                             20

<210> SEQ ID NO 33
<211> LENGTH: 20
<212> TYPE: DNA
<213> ORGANISM: artificial
<220> FEATURE:
<223> OTHER INFORMATION: oligonucleotide

<400> SEQUENCE: 33
gccgacctca tggggtacat                                             20

<210> SEQ ID NO 34
<211> LENGTH: 19
<212> TYPE: DNA
<213> ORGANISM: artificial
<220> FEATURE:
<223> OTHER INFORMATION: oligonucleotide

<400> SEQUENCE: 34
ggttgctctt tctctatct                                              19

<210> SEQ ID NO 35
<211> LENGTH: 19
<212> TYPE: DNA
<213> ORGANISM: artificial
<220> FEATURE:
<223> OTHER INFORMATION: oligonucleotide

<400> SEQUENCE: 35
```

```
gggatatgat gatgaactg                                                    19

<210> SEQ ID NO 36
<211> LENGTH: 19
<212> TYPE: DNA
<213> ORGANISM: artificial
<220> FEATURE:
<223> OTHER INFORMATION: oligonucleotide

<400> SEQUENCE: 36
ggatgaaccg gctaatagc                                                    19

<210> SEQ ID NO 37
<211> LENGTH: 19
<212> TYPE: DNA
<213> ORGANISM: artificial
<220> FEATURE:
<223> OTHER INFORMATION: oligonucleotide

<400> SEQUENCE: 37
ggagatgggc ggcaacatc                                                    19

<210> SEQ ID NO 38
<211> LENGTH: 19
<212> TYPE: DNA
<213> ORGANISM: artificial
<220> FEATURE:
<223> OTHER INFORMATION: oligonucleotide

<400> SEQUENCE: 38
gtcttcacgg aggctatga                                                    19

<210> SEQ ID NO 39
<211> LENGTH: 20
<212> TYPE: DNA
<213> ORGANISM: artificial
<220> FEATURE:
<223> OTHER INFORMATION: oligonucleotide

<400> SEQUENCE: 39
gtcaactcct ggctaggcaa                                                   20

<210> SEQ ID NO 40
<211> LENGTH: 20
<212> TYPE: DNA
<213> ORGANISM: artificial
<220> FEATURE:
<223> OTHER INFORMATION: oligonucleotide

<400> SEQUENCE: 40
gtccacagtt actctccagg                                                   20

<210> SEQ ID NO 41
<211> LENGTH: 20
<212> TYPE: DNA
<213> ORGANISM: artificial
<220> FEATURE:
<223> OTHER INFORMATION: oligonucleotide

<400> SEQUENCE: 41
gcctcttcaa ctgggcagta                                                   20

<210> SEQ ID NO 42
<211> LENGTH: 19
<212> TYPE: DNA
<213> ORGANISM: artificial
<220> FEATURE:
```

```
<223> OTHER INFORMATION: oligonucleotide

<400> SEQUENCE: 42
agcttaaact cactccaat                                              19

<210> SEQ ID NO 43
<211> LENGTH: 19
<212> TYPE: DNA
<213> ORGANISM: artificial
<220> FEATURE:
<223> OTHER INFORMATION: oligonucleotide

<400> SEQUENCE: 43
gctccatctt agccctagt                                              19

<210> SEQ ID NO 44
<211> LENGTH: 20
<212> TYPE: DNA
<213> ORGANISM: artificial
<220> FEATURE:
<223> OTHER INFORMATION: oligonucleotide

<400> SEQUENCE: 44
gtccatctta gccctagtca                                             20

<210> SEQ ID NO 45
<211> LENGTH: 19
<212> TYPE: DNA
<213> ORGANISM: artificial
<220> FEATURE:
<223> OTHER INFORMATION: oligonucleotide

<400> SEQUENCE: 45
gtcacggcta gctgtgaaa                                              19

<210> SEQ ID NO 46
<211> LENGTH: 19
<212> TYPE: DNA
<213> ORGANISM: artificial
<220> FEATURE:
<223> OTHER INFORMATION: oligonucleotide

<400> SEQUENCE: 46
acggctagct gtgaaaggt                                              19

<210> SEQ ID NO 47
<211> LENGTH: 19
<212> TYPE: DNA
<213> ORGANISM: artificial
<220> FEATURE:
<223> OTHER INFORMATION: oligonucleotide

<400> SEQUENCE: 47
gctgtgaaag gtccgtgag                                              19

<210> SEQ ID NO 48
<211> LENGTH: 19
<212> TYPE: DNA
<213> ORGANISM: artificial
<220> FEATURE:
<223> OTHER INFORMATION: oligonucleotide

<400> SEQUENCE: 48
ggtccgtgag ccgcatgac                                              19

<210> SEQ ID NO 49
```

```
<211> LENGTH: 20
<212> TYPE: DNA
<213> ORGANISM: artificial
<220> FEATURE:
<223> OTHER INFORMATION: oligonucleotide

<400> SEQUENCE: 49
gccgcatgac tgcagagagt                                              20

<210> SEQ ID NO 50
<211> LENGTH: 20
<212> TYPE: DNA
<213> ORGANISM: artificial
<220> FEATURE:
<223> OTHER INFORMATION: oligonucleotide

<400> SEQUENCE: 50
actggcctct ctgcagatca                                              20

<210> SEQ ID NO 51
<211> LENGTH: 19
<212> TYPE: DNA
<213> ORGANISM: artificial
<220> FEATURE:
<223> OTHER INFORMATION: oligonucleotide

<400> SEQUENCE: 51
tagccctagt cacggctag                                               19

<210> SEQ ID NO 52
<211> LENGTH: 19
<212> TYPE: DNA
<213> ORGANISM: artificial
<220> FEATURE:
<223> OTHER INFORMATION: oligonucleotide

<400> SEQUENCE: 52
agctgtgaaa ggtccgtga                                               19

<210> SEQ ID NO 53
<211> LENGTH: 19
<212> TYPE: DNA
<213> ORGANISM: artificial
<220> FEATURE:
<223> OTHER INFORMATION: oligonucleotide

<400> SEQUENCE: 53
tagctgtgaa aggtccgtg                                               19

<210> SEQ ID NO 54
<211> LENGTH: 19
<212> TYPE: DNA
<213> ORGANISM: artificial
<220> FEATURE:
<223> OTHER INFORMATION: oligonucleotide

<400> SEQUENCE: 54
ctagctgtga aaggtccgt                                               19

<210> SEQ ID NO 55
<211> LENGTH: 19
<212> TYPE: DNA
<213> ORGANISM: artificial
<220> FEATURE:
<223> OTHER INFORMATION: oligonucleotide

<400> SEQUENCE: 55
```

```
ctgtgaaagg tccgtgagc                                                 19

<210> SEQ ID NO 56
<211> LENGTH: 19
<212> TYPE: DNA
<213> ORGANISM: artificial
<220> FEATURE:
<223> OTHER INFORMATION: oligonucleotide

<400> SEQUENCE: 56
gaaaggtccg tgagccgca                                                 19

<210> SEQ ID NO 57
<211> LENGTH: 166
<212> TYPE: DNA
<213> ORGANISM: artificial
<220> FEATURE:
<223> OTHER INFORMATION: ApoE enhancer

<400> SEQUENCE: 57
agatctgctg tttgtgtgct gcctctgaag tccacactga acaaacttca gcctactcat    60
gtccctaaaa tgggcaaaca ttgcaagcag caaacagcaa acacacagcc ctccctgcct   120
gctgaccttg gagctggggc agaggtcaga gacctctctg agatct                  166

<210> SEQ ID NO 58
<211> LENGTH: 334
<212> TYPE: DNA
<213> ORGANISM: artificial
<220> FEATURE:
<223> OTHER INFORMATION: Synthetic Enhancer

<400> SEQUENCE: 58
agatctgtca attcacgcga gttaataatt accagcgcgg gccaaataaa taatccgcga    60
ggggcaggtg acgtttgccc agcgcgcgct ggtaattatt aacctcgcga atattgattc   120
gaggccgcga ttgccgcaat cgcgaggggc aggtgacctt gcccagcgc gcgttcgccc   180 cgccccggac ggtatcgatg tcgaggggga tcccactggg aggatgttga gtaagatgga   240
aaactactga tgacccttgc agagacagag tattaggaca tgtttgaaca ggggccgggc   300
gatcagcagg tagctctaga ggtaccccag atct                               334

<210> SEQ ID NO 59
<211> LENGTH: 355
<212> TYPE: DNA
<213> ORGANISM: artificial
<220> FEATURE:
<223> OTHER INFORMATION: hAAT promoter

<400> SEQUENCE: 59
agatctttgc taccagtgga acagccacta aggattctgc agtgagagca gagggccagc    60
taagtggtac tctcccagag actgtctgac tcacgccacc cctccacct tggacacagg   120 acgctgtggt ttctgagcca ggtacaatga ctcctttcgg taagtgcagt ggaagctgta   180
cactgcccag gcaaagcgtc cgggcagcgt aggcgggcga ctcagatccc agccagtgga   240
cttagcccct gtttgctcct ccgataactg gggtgacctt ggttaatatt caccagcagc   300 ctccccgtt gccctctgg taccactgct aaatacgga cgaggacagg gccag           355

<210> SEQ ID NO 60
<211> LENGTH: 560
<212> TYPE: DNA
<213> ORGANISM: artificial
<220> FEATURE:
```

<223> OTHER INFORMATION: LCAT promoter

<400> SEQUENCE: 60

```
agatctctgg gcctcaaaat ggagatggat cccaggtctt gtgggaccct gggatgtttg      60
gggactttac tatctagcac cccagtaggc ctgtcctggc cagagaagac tggtaggggc     120
cgagtggggt ttgaaggcag ccggcccggc ccagcccagg agcgctattt attgcatatt     180
tattgtttgg atgtcaccat cagagacgaa gggaagggta gccagggagg gagtccagcc     240
cagctgcctg caggagaatc tggctcagtc tactatgggc agggcccccc accaagctga     300
gccgaatgga gacagctgag ctgaggcctg acttttcaa taaaacattg tgtagttctg      360
ggcctcctgc tgccccggct ctgtttcccc tggcgccaag agaagaaggc ggaactgaac     420
ccaggcccag agccggctcc ctgaggctgt gccccttcc ggcaatctct ggccacaacc      480
cccactggcc aggccgtccc tcccactggc cctagggccc ctcccactcc cacaccagat     540
aaggacagcc cagtgccgtc                                                  560
```

<210> SEQ ID NO 61
<211> LENGTH: 405
<212> TYPE: DNA
<213> ORGANISM: artificial
<220> FEATURE:
<223> OTHER INFORMATION: ApoH promoter

<400> SEQUENCE: 61

```
agatctgaga gtaggtgttt gtccaaagtt tatatgccaa ggctgtgagt gaaacaggag      60
cttcgatctt ttggtgttcc atctacaaca tacacaaaac aaaagatgga gaatgagaag    120
tccaggcaac cccggaaaca acaagtttct gtcaaaagca ataatgaact gttttgtgcc    180
attaacaaaa acgttatgaa gacagaaacc atctcccaaa gatttcataa cagagccaca    240
taagtggaaa gtaaatgatt aaagaatgtg ggtctcagag ttccattcaa atcatgatac    300
tttatcttct atttacaaag ataaagtac accagaaaat ggttaatgtt taagcgcttt      360
catatttggc tctgtctttt tagcagacga aaaccacttt ggcag                     405
```

<210> SEQ ID NO 62
<211> LENGTH: 240
<212> TYPE: DNA
<213> ORGANISM: artificial
<220> FEATURE:
<223> OTHER INFORMATION: Transthyretin promoter

<400> SEQUENCE: 62

```
agatctagtg tctgtctgca catttcgtag agcgagtgtt ccgatactct aatctcccta     60
ggcaaggttc atatttgtgt aggttactta ttctcctttt gttgactaag tcaataatca   120
gaatcagcag gtttggagtc agcttggcag ggatcagcag cctgggttgg aaggaggggg   180
tataaaagcc ccttcaccag gagaagccca gctgcccggg gttatagtca gatgactagt   240
```

<210> SEQ ID NO 63
<211> LENGTH: 663
<212> TYPE: DNA
<213> ORGANISM: artificial
<220> FEATURE:
<223> OTHER INFORMATION: fusion promoter with ApoE-hepatic control
      region (HCR) enhancer and hAATpromoter

<400> SEQUENCE: 63

```
gtttctgggc tcaccctgcc cccttccaac ccctcagttc ccatcctcca gcagctgttt     60
gtgtgctgcc tctgaagtcc acactgaaca aacttcagcc tactcatgtc cctaaaatgg   120
```

-continued

```
gcaaacattg caagcagcaa acagcaaaca cacagccctc cctgcctgct gaccttggag    180
ctggggcaga ggtcagagac ctctctgggc ccatgccacc tccaacatcc actcgacccc    240
ttggaatttc ggtggagagg agcagaggtt gtcctggcgt ggtttaggta gtgtgagagg    300
ggtacccggg gatcttgcta ccagtggaac agccactaag gattctgcag tgagagcaga    360
gggccagcta agtggtactc tcccagagac tgtctgactc acgccacccc ctccaccttg    420
gacacaggac gctgtggttt ctgagccagg tacaatgact cctttcggta agtgcagtgg    480
aagctgtaca ctgcccaggc aaagcgtccg ggcagcgtag gcgggcgact cagatcccag    540
ccagtggact tagcccctgt ttgctcctcc gataactggg gtgaccttgg ttaatattca    600
ccagcagcct cccccgttgc ccctctggat ccactgctta aatacggacg aggacagggc    660
cct                                                                  663

<210> SEQ ID NO 64
<211> LENGTH: 57
<212> TYPE: DNA
<213> ORGANISM: artificial
<220> FEATURE:
<223> OTHER INFORMATION: oligonucleotide

<400> SEQUENCE: 64
gaacaaatgg cactagtaaa ctgagtcaag agctcagttt actagtgcca tttgttc        57
```

RNAI EXPRESSION CONSTRUCTS WITH LIVER-SPECIFIC ENHANCER/PROMOTER

CROSS-REFERENCE TO RELATED APPLICATIONS

This application claims benefit of U.S. Provisional Patent Application Ser. No. 60/653,616, filed Feb. 16, 2005 which is herein incorporated by reference.

GOVERNMENT RIGHTS IN THIS INVENTION

This invention was made with U.S. government support under grant number AI40034 from the National Institutes of Health (NIH). The U.S. government has certain rights in this invention.

BACKGROUND OF THE INVENTION

Utilization of double-stranded RNA to inhibit gene expression in a sequence-specific manner has revolutionized the drug discovery industry. In mammals, RNA interference, or RNAi, is mediated by 15- to 49-nucleotide long, double-stranded RNA molecules referred to as small interfering RNAs (RNAi agents). RNAi agents can be synthesized chemically or enzymatically outside of cells and subsequently delivered to cells (see, e.g., Fire, et al., *Nature*, 391: 806-11 (1998); Tuschl, et al., *Genes and Dev.*, 13:3191-97 (1999); and Elbashir, et al., *Nature*, 411:494-498 (2001)); or can be expressed in vivo by an appropriate vector in cells (see, e.g., U.S. Pat. No. 6,573,099).

In vivo delivery of unmodified RNAi agents as an effective therapeutic for use in humans faces a number of technical hurdles. First, due to cellular and serum nucleases, the half life of RNA injected in vivo is only about 70 seconds (see, e.g., Kurreck, *Eur. J. Bioch.* 270:1628-44 (2003)). Efforts have been made to increase stability of injected RNA by the use of chemical modifications; however, there are several instances where chemical alterations led to increased cytotoxic effects. In one specific example, cells were intolerant to doses of an RNAi duplex in which every second phosphate was replaced by phosphorothioate (Harborth, et al., *Antisense Nucleic Acid Drug Rev.* 13(2): 83-105 (2003)). Other hurdles include providing tissue-specific delivery, as well as being able to deliver the RNAi agents in amounts sufficient to elicit a therapeutic response, but that are not toxic.

Several options are being explored for RNAi delivery, including the use of viral-based and non-viral based vector systems that can infect or otherwise transfect target cells, and deliver and express RNAi molecules in situ. Often, small RNAs are transcribed as short hairpin RNA (shRNA) precursors from a viral or non-viral vector backbone. Once transcribed, the shRNA precursors are processed by the enzyme Dicer into the appropriate active RNAi agents. Viral-based delivery approaches attempt to exploit the targeting properties of viruses to generate tissue specificity and once appropriately targeted, rely upon the endogenous cellular machinery to generate sufficient levels of the RNAi agents to achieve a therapeutically effective dose.

One useful application of RNAi therapeutics is to deliver therapeutics to the liver to treat liver-specific diseases and infections. Thus, there is a need in the art to develop a way to deliver stable, effective, expressed RNAi agents in a liver-specific manner. The present invention satisfies this need in the art.

SUMMARY OF THE INVENTION

The present invention is directed to genetic constructs for delivering RNAi agents specifically to the liver to treat various diseases or disorders. In one aspect, the present invention provides innovative nucleic acid molecules that are expression constructs comprising one or more Apo Lipoprotein E enhancer elements ("ApoE" or "ApoE enhancer"), one or more liver-specific promoters ("livpro"), and one or more RNAi constructs that provide one or more RNAi agents for modifying target gene expression in the liver. In another aspect, the present invention provides an expression cassette (hereinafter referred to as an ApoE/livpro RNAi expression cassette) comprising one or more ApoE enhancer elements, one or more liver-specific promoters and one or more RNAi constructs that provide one or more RNAi agents, preferably where the RNAi agents are expressed as stem-loop structures, also referred to as short hairpin RNAs (shRNAs), and preferably where there are two to seven additional nucleotides between the transcription initiation point and the first nucleotide of the RNAi construct.

In some embodiments of the present invention, the ApoE/livpro RNAi expression cassette comprises one or more ApoE enhancers and one liver-specific promoter driving the expression of one RNAi agent. In other embodiments, the ApoE/livpro RNAi expression cassette comprises one or more ApoE enhancers and one liver-specific promoter driving the expression of more than one RNAI agent. In yet other embodiments, the ApoE/livpro RNAi expression cassette comprises one or more ApoE enhancers and one liver-specific promoter driving the expression of one RNAi agent, but there are two or more ApoE/livpro/RNAi components in the expression cassette.

In another aspect, a method of modifying the expression of one or more genes in the liver, comprising delivering to the liver an expression construct comprising one or more enhancer elements selected from the group consisting of ApoE enhancer elements and SynEnh enhancer elements, one or more liver-specific promoters, and one or more RNAi constructs that provide one or more RNAi agents.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments that are illustrated in the appended drawings. It is to be noted, however, that the appended drawings illustrate only certain embodiments of this invention and are therefore not to be considered limiting of its scope, for the present invention may admit to other equally effective embodiments.

FIGS. 4A and 4B show two embodiments of multiple expression ApoE/livpro RNAi expression cassettes that deliver the RNAi agents as siRNAs, and FIGS. 4C and 4D show embodiments of multiple-promoter ApoE/livpro RNAi expression cassettes that deliver RNAi agents as shRNA precursors.

FIG. 8B also shows data that compares hAAT promoter efficiency with strong, ubiquitously U6 pol III promoter efficiency.

FIG. 11A shows the sAg levels of three different mice injected with the $1×10^{11}$ (lo) dose of particles of dsAAV8-packaged expression cassettes for ApoE/hAAT-driven, U1 3'box-terminated hairpins against luciferase (luc). FIG. 11B shows the sAg levels of three different mice injected with the $1×10^{11}$ (lo) dose of particles of dsAAV8-packaged expression cassettes for ApoE/hAAT-driven, U1 3'box-terminated hairpins against HBV sAg (25mer). FIG. 11C shows the sAg levels of three different mice injected with the $3×10^{11}$ (hi) dose of particles of dsAAV8-packaged expression cassettes for ApoE/hAAT-driven, U1 3'box-terminated hairpins against luciferase (luc). FIG. 11D shows the sAg levels of three different mice injected with the 3×10$^{11}$ (hi) dose of particles of dsAAV8-packaged expression cassettes for ApoE/hAAT-driven, U1 3'box-terminated hairpins against HBV sAg (25mer).

DETAILED DESCRIPTION

Figure 1A:
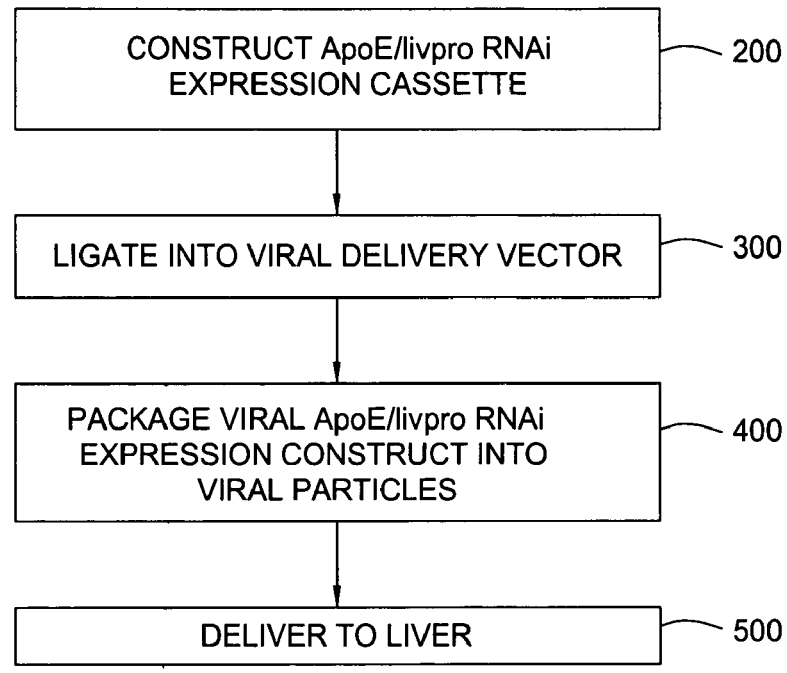
FIG. 1A is a simplified block diagram of one embodiment for delivering ddRNAi agents to the liver according to the present invention via a viral vector.

Before the present compositions and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

As used herein, the singular forms "a," "an," and "the" include plural referents unless the context clearly dictates otherwise. Thus, for example, reference to "a factor" refers to one or mixtures of factors, and reference to "the method of production" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference, without limitation, for the purpose of describing and disclosing devices, formulations and methodologies which are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The present invention is directed to innovative, robust genetic compositions and methods to treat diseases or disorders of the liver using novel RNAi cassettes.

Generally, conventional methods of molecular biology, microbiology, recombinant DNA techniques; cell biology, and virology within the skill of the art are employed in the present invention. Such techniques are explained fully in the literature, see, e.g., Maniatis, Fritsch & Sambrook, *Molecular Cloning: A Laboratory Manual* (1982); *DNA Cloning: A Practical Approach*, Volumes I and II (D. N. Glover, ed. 1985); *Oligonucleotide Synthesis* (M. J. Gait, ed. 1984); *Nucleic Acid Hybridization* (B. D. Hames & S. J. Higgins, eds. (1984)); *Animal Cell Culture* (R. I. Freshney, ed. 1986); and *RNA Viruses: A practical Approach*, (Alan, J. Cann, Ed., Oxford University Press, 2000).

A "vector" is a replicon, such as plasmid, phage, viral construct or cosmid, to which another DNA segment may be attached. Vectors are used to transduce and express the DNA segment in cells.

A "promoter" or "promoter sequence" is generally a DNA regulatory region capable of binding RNA polymerase in a cell and initiating transcription of a polynucleotide or polypeptide coding sequence such as messenger RNA, ribosomal RNAs, small nuclear or nucleolar RNAs or any kind of RNA transcribed by any class of any RNA polymerase.

A cell has been "transformed", "transduced" or "transfected" by an exogenous or heterologous nucleic acid or vector when such nucleic acid has been introduced inside the cell, for example, as a complex with transfection reagents or packaged in viral particles. The transforming DNA may or may not be integrated (covalently linked) into the genome of the cell. With respect to eukaryotic cells, a stably transformed cell is one in which the transforming DNA has become integrated into a host cell chromosome or is maintained extra-chromosomally so that the transforming DNA is inherited by daughter cells during cell replication or is a non-replicating, differentiated cell in which a persistent episome is present.

The term "RNA interference" or "RNAi" refers generally to a process in which a double-stranded RNA molecule changes the expression of a nucleic acid sequence with which the double-stranded RNA molecule shares substantial or total homology. The term "RNAi agent" refers to an RNA sequence that elicits RNAi; the term "RNAi construct" refers to a nucleic acid sequence that encodes an RNAi agent or is transcribed to provide an RNAi agent; and the term "ddRNAi agent" refers to an RNAi agent that is transcribed from a vector. The terms "short hairpin RNA" or "shRNA" refer to an RNA structure having a duplex region and a loop region. In some embodiments of the present invention, ddRNAi agents are expressed initially as shRNAs.

The term "liver-specific promoter" or, shorthand, "livpro", refers to a promoter that initiates transcription of a polynucleotide selectively in the liver. The term "ApoE/livpro RNAi expression cassette" refers to a cassette according to embodiments of the present invention having one or more ApoE enhancer elements, one or more liver-specific promoters and one or more RNAi constructs that provide one or more RNAi agents. The RNAi agents preferably are expressed initially as shRNAs, but in some embodiments may be expressed as single-stranded complementary RNAs. The terms "ApoE/livpro RNAi expression construct" or "ApoE/livpro RNAi expression vector" refer to viral or non-viral vectors containing a ApoE/livpro RNAi expression cassette.

"Derivatives" of a gene or nucleotide sequence refers to any isolated nucleic acid molecule that contains significant sequence similarity to the gene or nucleotide sequence or a part thereof. In addition, "derivatives" include such isolated nucleic acids containing modified nucleotides or mimetics of naturally-occurring nucleotides.

Figure 1B:
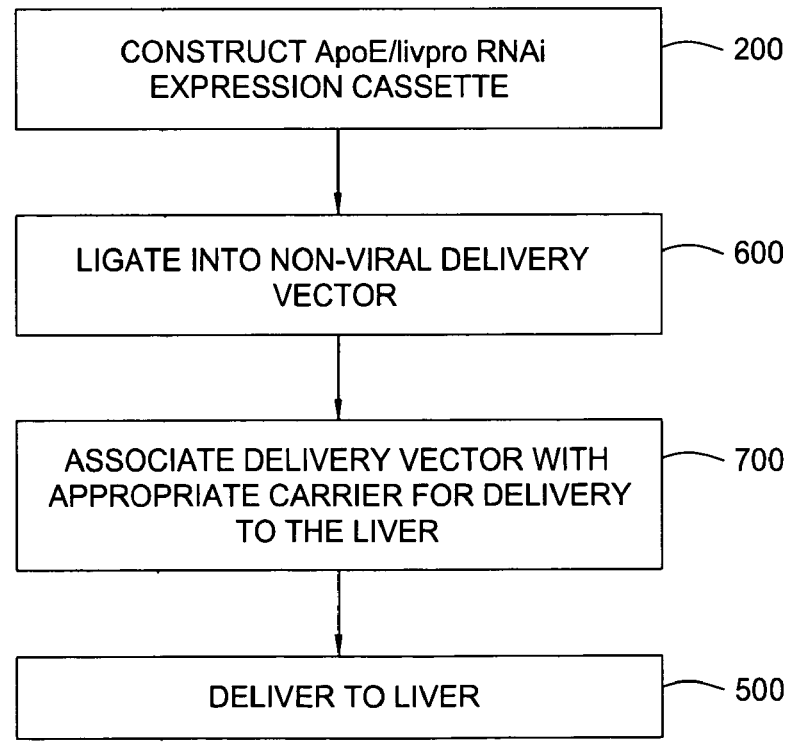
FIG. 1B is a simplified block diagram of one embodiment for delivering ddRNAi agents to the liver according to the present invention via a non-viral vector.

FIG. 1A is a simplified flow chart showing the steps of a method according to one embodiment of the present invention in which an ApoE/livpro RNAi expression construct may be used. The method includes a step 200 in which the ApoE/livpro RNAi expression cassette targeting diseases or disorders of the liver is constructed. Next, in step 300, the ApoE/livpro RNAi expression cassette is ligated into an appropriate viral delivery construct. The viral ApoE/livpro RNAi expression delivery construct is then packaged into viral particles at step 400, and the viral particles are delivered to the liver at step 500. Details for each of these steps and the components involved are presented infra. FIG. 1B is a simplified flow chart showing the steps of another method according to one embodiment of the present invention in which an ApoE/livpro RNAi expression construct may be used. The method shown in FIG. 1B also includes a step 200 in which the ApoE/livpro RNAi expression cassette targeting diseases or disorders of the liver is constructed. However, in this embodiment, the ApoE/livpro RNAi expression cassette is ligated into an appropriate non-viral delivery construct at step 600. Next, in step 700, the non-viral ApoE/livpro RNAi expression construct is associated with an appropriate carrier for delivery of the non-viral ApoE/livpro RNAi expression construct to the liver. Finally, in step 500, the non-viral ApoE/livpro RNAi expression construct is delivered to the liver.

ApoE/livpro RNAi expression constructs according to the present invention can be generated synthetically or enzymatically by a number of different protocols known to those of skill in the art and purified using standard recombinant DNA techniques as described in, for example, Sambrook et al., *Molecular Cloning: A Laboratory Manual,* 2nd Ed., Cold Spring Harbor Press, Cold Spring Harbor, N.Y. (1989), and under regulations described in, e.g., United States Dept. of HHS, National Institute of Health (NIH) Guidelines for Recombinant DNA Research.

Figure 9:
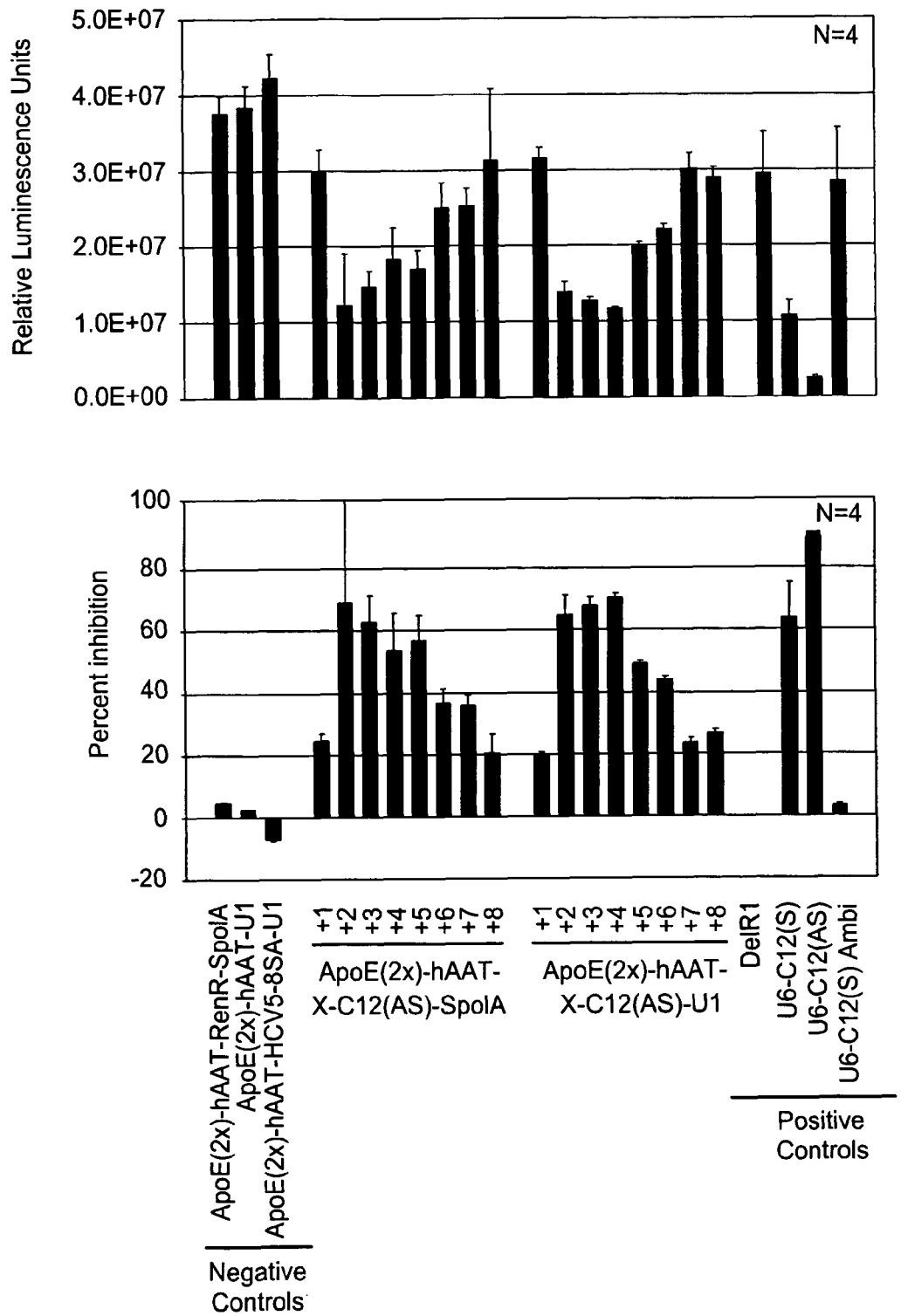
FIG. 9A shows the sequence (AGATCTGCTGTTTGTGT-GCTGCCTCTGAAGTCCACACTGAA-CAAACTTCAGCC TACTCATGTC-CCTAAAATGGGCAAACATTGCAAGCAGCAAACAGC AAACACACA GCCCTCCCTGCCTGCTGACCTTG-GAGCTGGGGCAGAGGTCAGAGACCTCTCT GAGATCT; SEQ ID NO: 57) of one embodiment of a single ApoE enhancer according to the present invention.
FIG. 9B shows the sequence (AGATCTGTCAATTCACGCGAGT-TAATAATTACCAGCGCGGGCCAAATAAATAAT CCGCGAGGGGCAGGTGACGTTTGC-CCAGCGCGCGCTGGTAATTATTAACCTC GCGAATAT-TGATTCGAGGCCGCGATTGCCG-CAATCGCGAGGGGCAGGTGACC TTTGCCCAGCGCGCGTTCGCCCCGC-CCCGGACGGTATCGATGTCGAGGGGGA TCCCACTGGGAGGATGTTGAGTAAGATG-GAAAACTACTGATGACCCTTGCAGA GACAGAG-TATTAGGACATGTTTGAACAGGGGC-CGGGCGATCAGCAGGTAGCT CTAGAGGTACCCCAGATCT; SEQ ID NO: 58) of one embodiment of a synthetic enhancer.
FIG. 9c shows the sequence (AGATCTTTGCTACCAGTGGAACAGCCAC-TAAGGATTCTGCAGTGAGAGCAGAG GGC-CAGCTAAGTGGTACTCTCCCAGAGACT-GTCTGACTCACGCCACCCCTCC ACCTTGGACACAGGACGCTGTGGTTTCT-GAGCCAGGTACAATGACTCCTTTCG GTAAGTG-CAGTGGAAGCTGTACACTGCCCAG-GCAAAGCGTCCGGGCAGCGTA GGCGGGCGACTCAGATCCCAGCCAGTG-GACTTAGCCCCTGTTTGCTCCTCCG ATAACTGGGGTGACCTTGGTTAATAT-TCACCAGCACCTCCCCGTTGCCCCT CTGGTAC-CACTGCTTAAATACGGACGAGGACAGGGCCAG; SEQ ID NO: 59) of one embodiment of a hAAT promoter according to the present invention.
FIG. 9D shows the sequence (AGATCTCTGGGCCTCAAAATGGAGATG-GATCCCAGGTCTTGTGGGACCCTGG GATGTTTGGG-GACTTTCTATCTAGCACCCCAGTAGGC-CTGTCCTGGCCAGAG AAGACTGGTAGGGGC-CGAGTGGGGTTTGAAGGCAGCCGGCCCG-GCCCAGCC CAGGAGCGCTATTTATTGCATATTTAT-TGTTTGGATGTCACCATCAGAGACGAA GGGAAGGGTAGCCAGGGAGGGAGTC-CAGCCCAGCTGCCTGCAGGAGAATCT GGCT-CAGTCTACTATGGGCAGGGCCCCCCAC-CAAGCTGAGCCGAATGGAGAC AGCTGAGCTGAGGCCT-GACTTTTTCAATAAAACATTGTGTAGT-TCTGGGCCTCC TGCTGCCCCGGCTCTGTTTC-CCCTGGCGCCAAGAGAAGAAGGCGGAACTGAA CCCAGGCCCAGAGCCGGCTCCCTGAG-GCTGTGCCCCTTTCCGGCAATCTCTG GCCACAAC-CCCCACTGGCCAGGCCGTCCCTC-CCACTGGCCCTAGGGCCCCTC CCACTCCCACACCAGATAAGGACAGC-CCAGTGCCGTC; SEQ ID NO: 60) of one embodiment of an LCAT promoter according to the present invention.
FIG. 9E shows the sequence (AGATCTGAGAGTAGGT-GTTTGTCCAAAGTTTATATGCCAAGGCT-GTGAGTGAA ACAGGAGCTTCGATCTTTTGGTGTTC-CATCTACAACATACACAAAACAAAAGAT GGAGAATGAGAAGTCCAGGCAACCCCG-GAAACAACAAGTTTCTGTCAAAAGCA ATAAT-GAACTGTTTGTGCCATTAACAAAAACGT-TATGAAGACAGAAACCATCTC CCAAAGATTTCATAACAGAGCCACAT-AAGTGGAAAGTAAATGATTAAAGAATGT GGGTCT-CAGAGTTCCATTCAAATCATGATACTT-TATCTTCTATTTACAAAGATAA AAGTACACCAGAAAATGGTTAATGTT-TAAGCGCTTTCATATTTGGCTCTGTCTTT TTAGCA-GACGAAAACCACTTTGGCAG; SEQ ID NO: 61) of one embodiment of ApoH promoter according to the present invention
FIG. 9F shows the sequence (AGATCTAGT-GTCTGTCTGCACATTTCGTAGAGCGAGT-GTTCCGATACTCTAATC TCCCTAGGCAAGGT-TCATATTTGTGTAGGTTACTTATTCTCCTTTTGTTGAC TAA GTCAATAATCAGAATCAGCAGGTTTG-GAGTCAGCTTGGCAGGGATCAGCAGCC TGGGTTG-GAAGGAGGGGGTATAAAAGCCCCTTCAC-CAGGAGAAGCCCAGCTG CCCGGGGTTATAGTCAGATGACTAGT; SEQ ID NO: 62) of one embodiment of the prealbumin, aka the Transthyretin (TTR), promoter.
Figure 10:
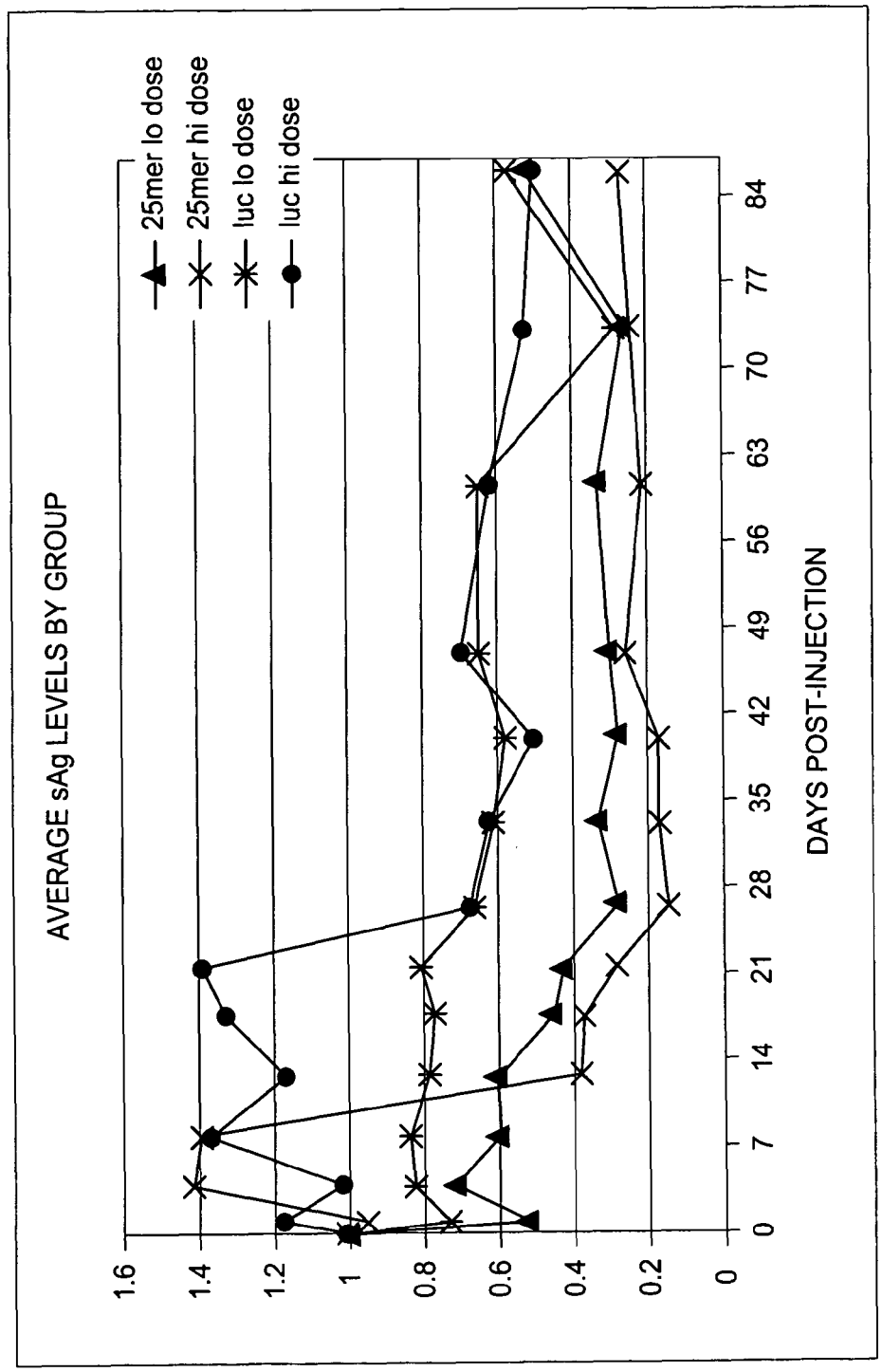
FIG. 10 shows the average hepatitis B virus s-antigen (sAg) levels as a fraction of the starting level (before injection) for transgenic HBV mice over a time course through 88 days post-injection. Mice received either $1×10^{11}$ (lo) or $3×10^{11}$ (hi) viral particles of dsAAV8-packaged expression cassettes for ApoE/hAAT-driven, U1 3'box-terminated hairpins against HBV sAg (25mer) or luciferase (luc, negative control).
Figure 11A:
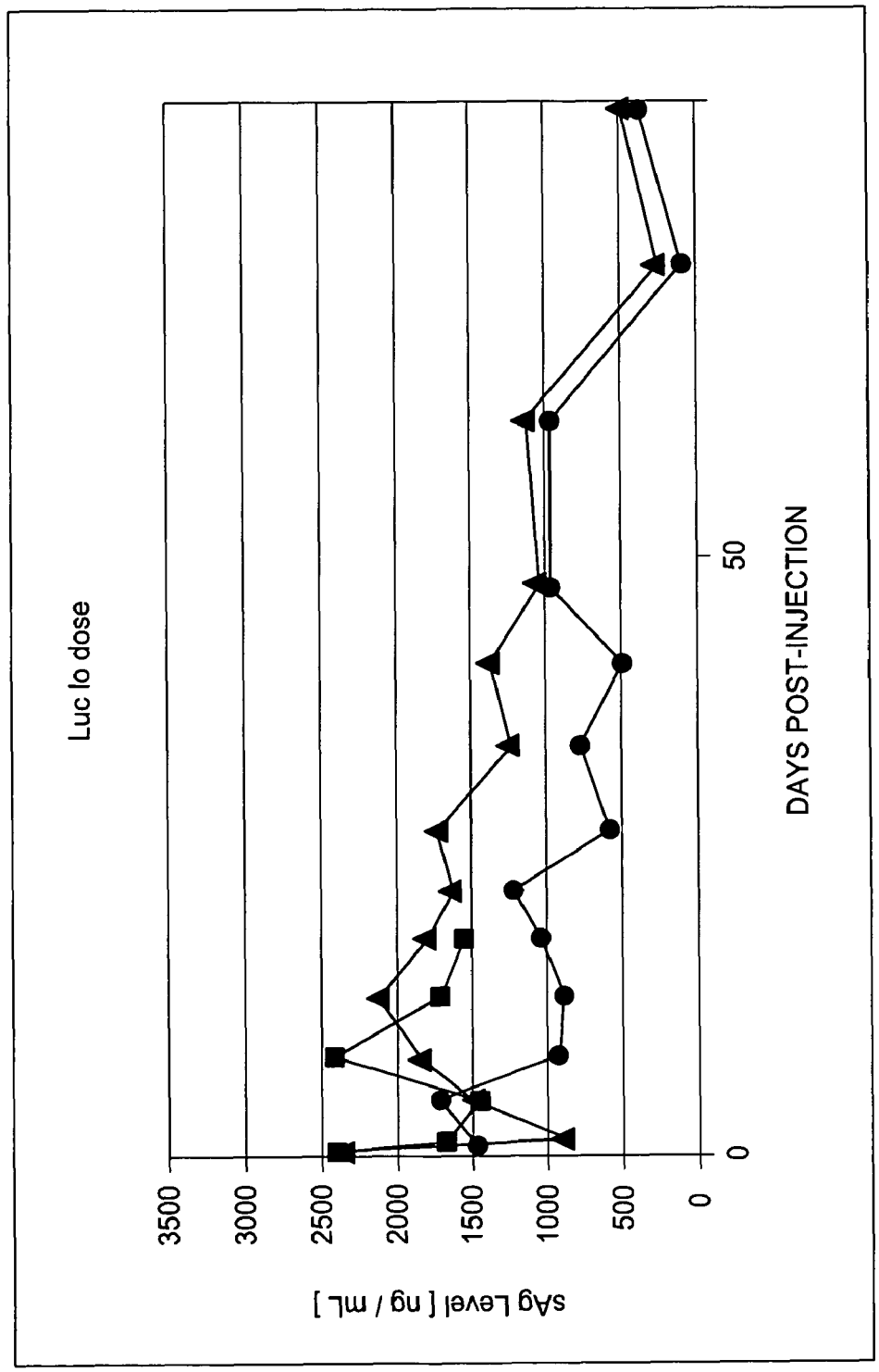
FIG. 11A-D show the sAg levels in ng/mL as measured by ELISA over the 88 day time course of FIG. 10.
Figure 11B:
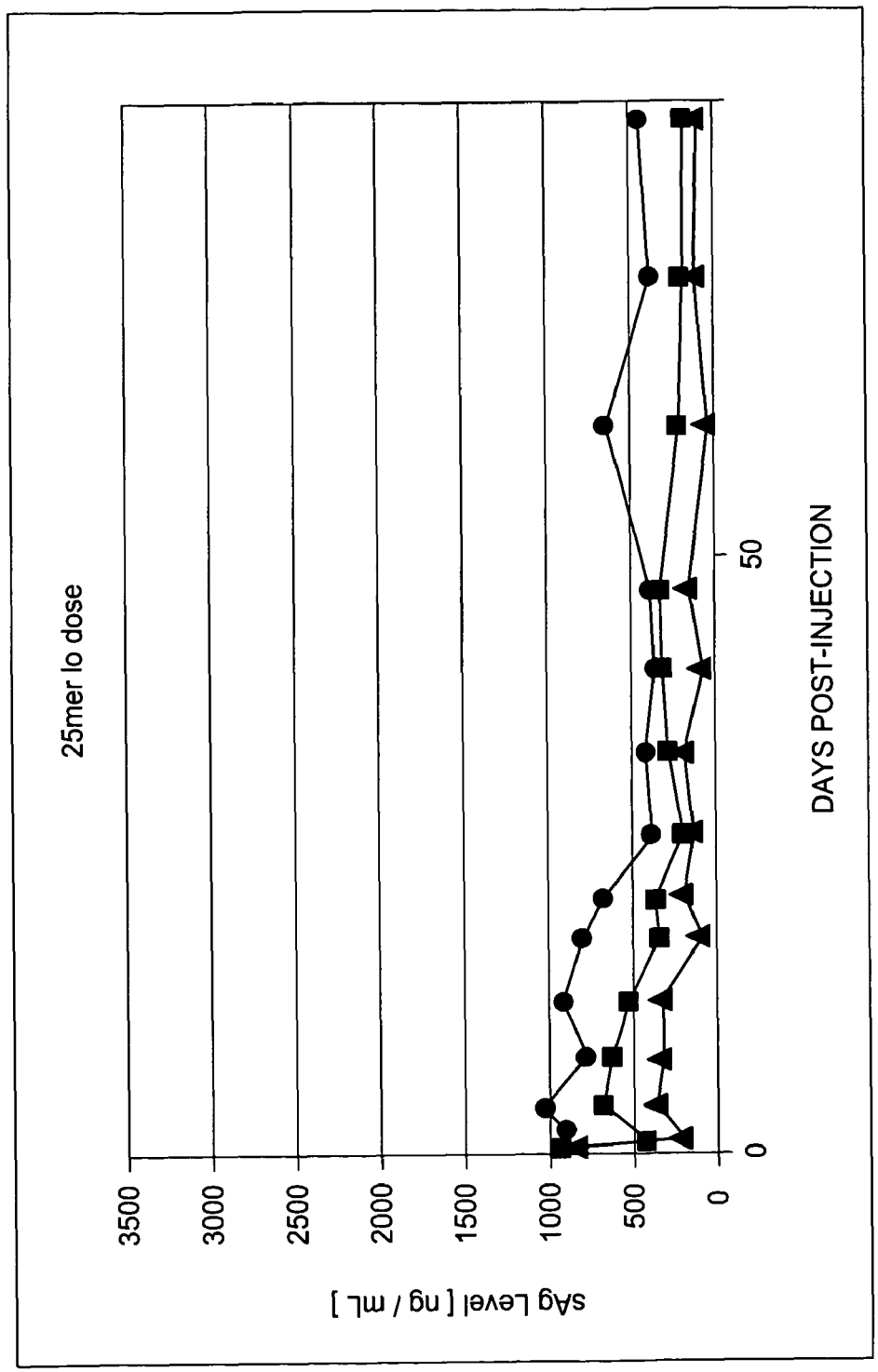
Figure 11C:
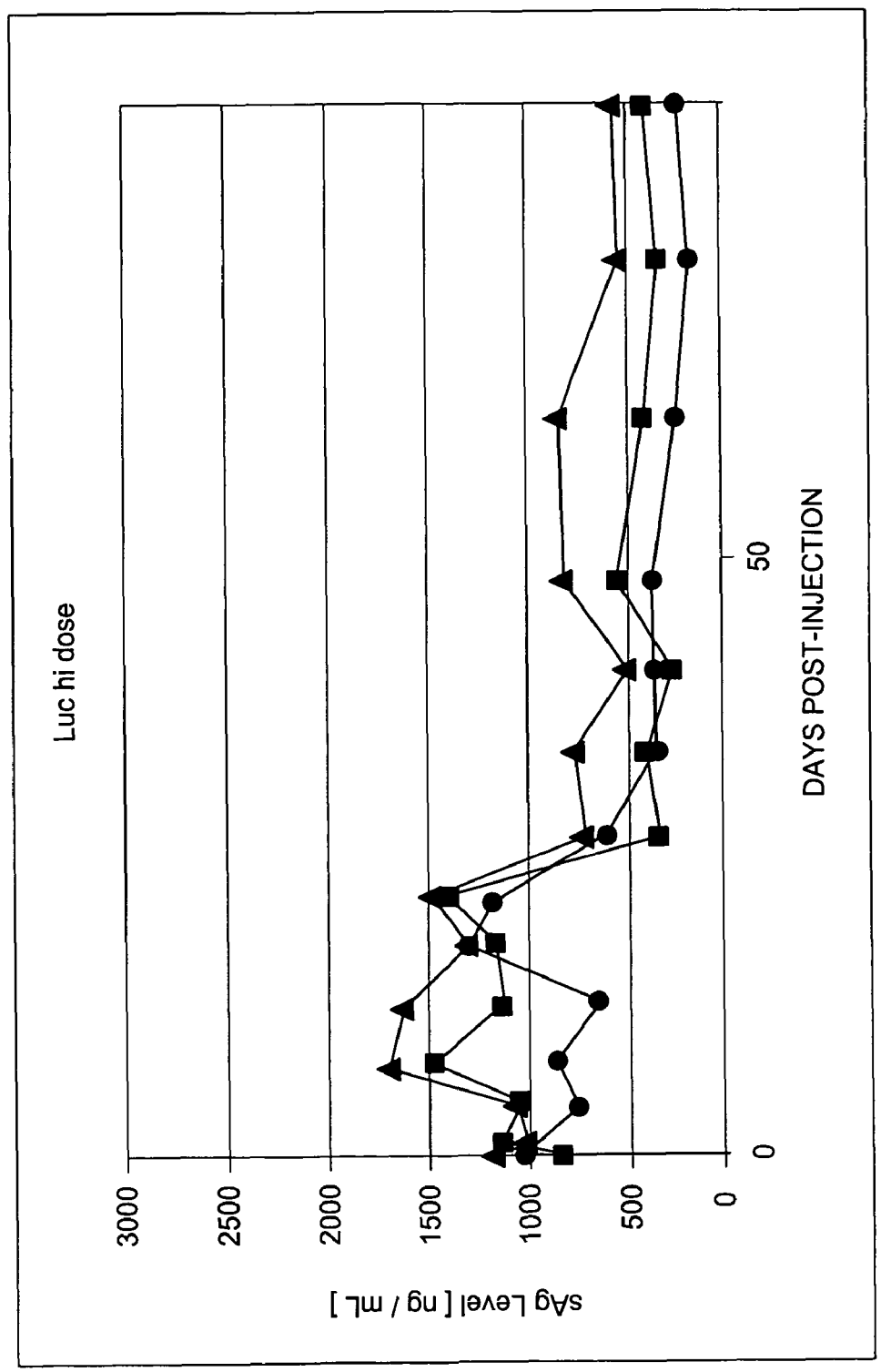
Figure 11D:
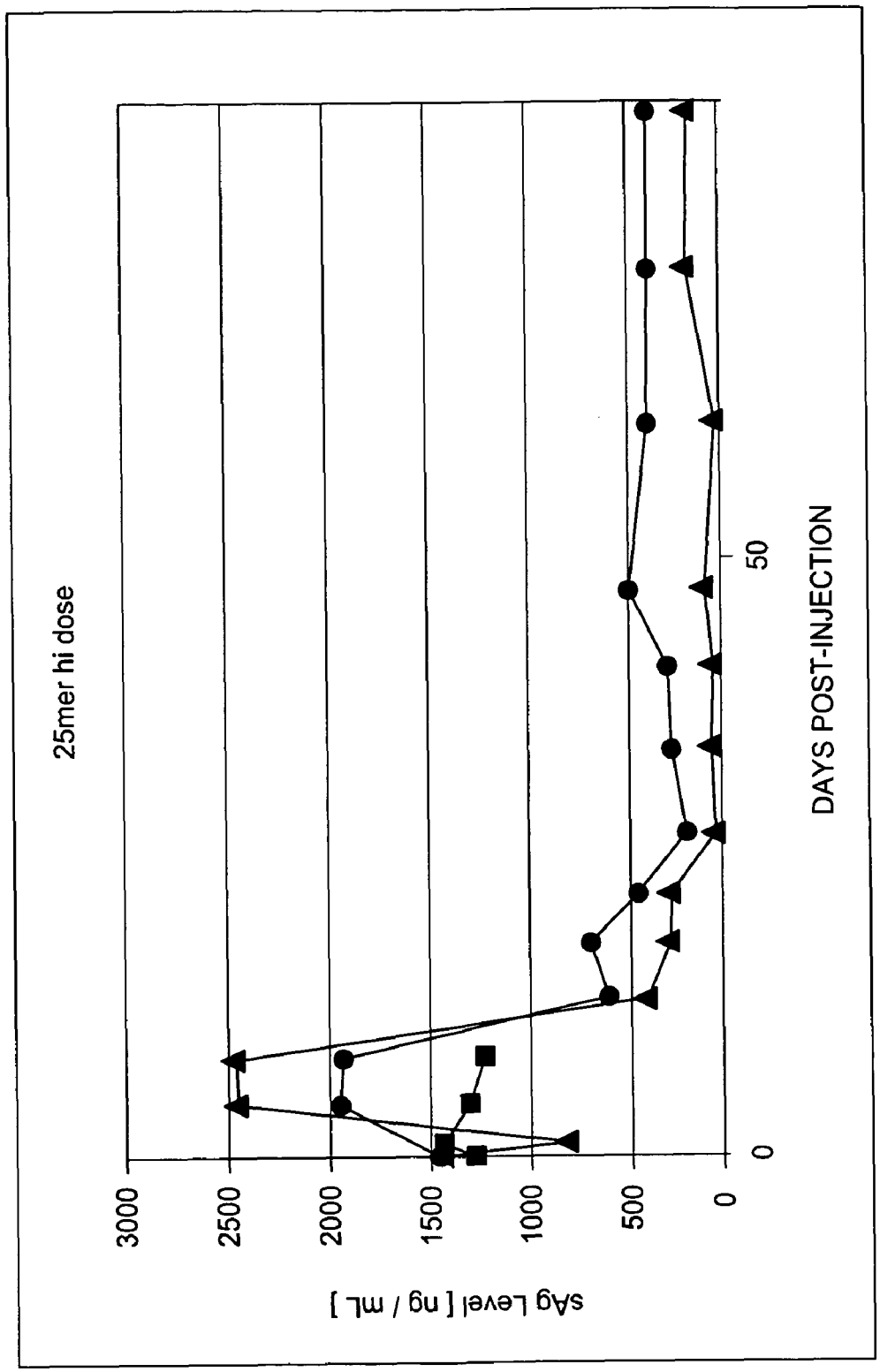

The ApoE enhancer element of the present invention is an enhancer element of approximately 155 bp derived from apolipoprotein E or ApoE. ApoE is an apolipoprotein that mediates binding, internalization and catabolism of lipoprotein particles and is a ligand for the low-density lipoprotein (ApoB/E) receptor and for the ApoE receptor of hepatic tissues. The genetic enhancer associated with the ApoE gene is a eukaryotic control element that can increase transcription of a nucleic acid specifically in the liver. The ApoE enhancer of the present invention may be located up to 2000 nucleotides upstream or downstream of the liver-specific promoter, and may be present in one or more copies. The sequence of one ApoE enhancer useful in the present invention is shown in FIG. 9A.

Although embodiments of the invention are described primarily with respect to constructs in which the enhancer is the ApoE ehancer, in any of the embodiments provided herein, the enhancer may be synthetic (SynEnh) instead. The synthetic enhancer (SynEnh) which has a total length of 577 basepairs has been described in detail in U.S. Pat. No. 6,808, 905 and was used to drive the expression of human factor VIII. It consist of three parts: a series of liver specific protein binding sites, an enhancer and a promoter.

As described in this invention the SynEnh has a total length of 330 basepairs. The first 210 bp consist of a series of binding sites for activator proteins specific to the liver such as hepatocyte nuclear factors 1 (2 copies), 3, 4 (2 copies) and 6 as well as binding sites for the Enhancer Binding Protein (EBP) and the transcription factor SP1. The remaining 120 nucleotides are made up of the natural (=wildtype) enhancer of the transthyretin promoter. The sequence of the SynEnh used in this invention is shown in FIG. 9B.

One liver-specific promoter useful in the methods and compositions of the present invention is a promoter derived from the human alpha-1 antitrypsin (hAAT) gene. Human alpha-1 antitrypsin is a major alpha-globulin, normally present in human plasma that inhibits many serine proteases, including trypsin, but especially elastase. The concentration of alpha-1 antitrypsin rises dramatically in response to infection or tissue injury. The hAAT promoter is a Pol II promoter approximately 600 nucleotides in length. The sequence of one hAAT promoter useful in the present invention is shown in FIG. 9C.

Another liver-specific promoter useful in the methods and compositions of the present invention is a promoter derived from the lecithin-cholesterol acyl transferase (LCAT) gene. LCAT is an enzyme that catalyzes a reaction between phosphatidylcholine and cholesterol to form a cholesteryl ester and 1-acylglyderophosphocholine. LCAT is central to the extracellular metabolism of plasma lipoproteins, and is approximately 590 nucleotides in length. The sequence of one LCAT promoter useful in the present invention is shown in FIG. 9D.

Yet another liver-specific promoter useful in the methods and compositions of the present invention is a promoter derived from the apolipoprotein H (ApoH) gene. ApoH is an apolioprotein that binds to anions such as heparin and phospholipids, as well as being an inhibitor of activated protein C. ApoH may present activation of the intrinsic blood coagulation cascade by binding to phospholipids on the surface of damaged cells. ApoH promoters are approximately 400 nucleotides in length, and the sequence of one ApoH promoter useful in embodiments of the present invention is shown in FIG. 9E.

Yet another liver-specific promoter useful in the methods and compositions of the present invention is a promoter derived from the mouse prealbumin gene. Prealbumin is a protein status indicator and a serum transport protein for thyroxin and retinol-binding protein. The half life of prealbumin is approximately 2 days, making prealbumin a more timely and sensitive indicator of protein status. Prealbumin is a tryptophan-rich protein, and like albumin, it is synthesized in the hepatocytes of the liver. Prealbumin's main function is to serve as a binding and transport protein. The more accurate name for prealbumin is transthyretin. FIG. 9F shows the sequence of the transthyretin promoter.

Figure 2:
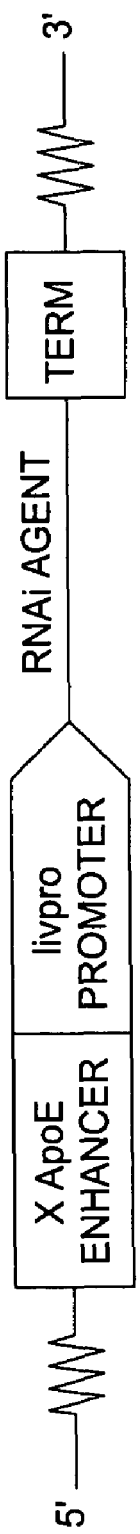
FIG. 2 is a simple embodiment of one ApoE/livpro RNAi expression cassette according to the present invention that delivers a single RNAi agent.

FIG. 2 shows a simple embodiment of one ApoE/livpro RNAi expression cassette according to the present invention. In this embodiment the following genetic elements appear 5' to 3': an ApoE enhancer, a liver-specific promoter, one RNAi agent and a termination sequence. It should be understood, however, that the ApoE enhancer element represented in this ApoE/livpro RNAi expression cassette and in other ApoE/livpro RNAi expression cassettes herein may comprise one ApoE enhancer sequence (approximately 155 bps), or two or more ApoE enhancer sequences.

Figure 3A:
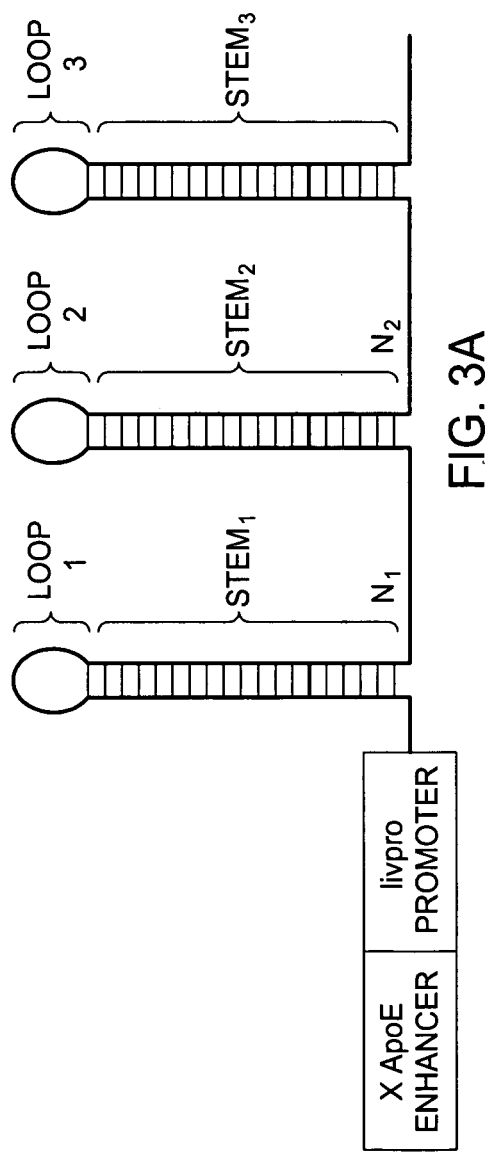
FIGS. 3A and 3B show two different embodiments of ApoE/livpro RNAi expression cassettes according to the present invention that deliver multiple RNAi agents simultaneously.
Figure 3B:
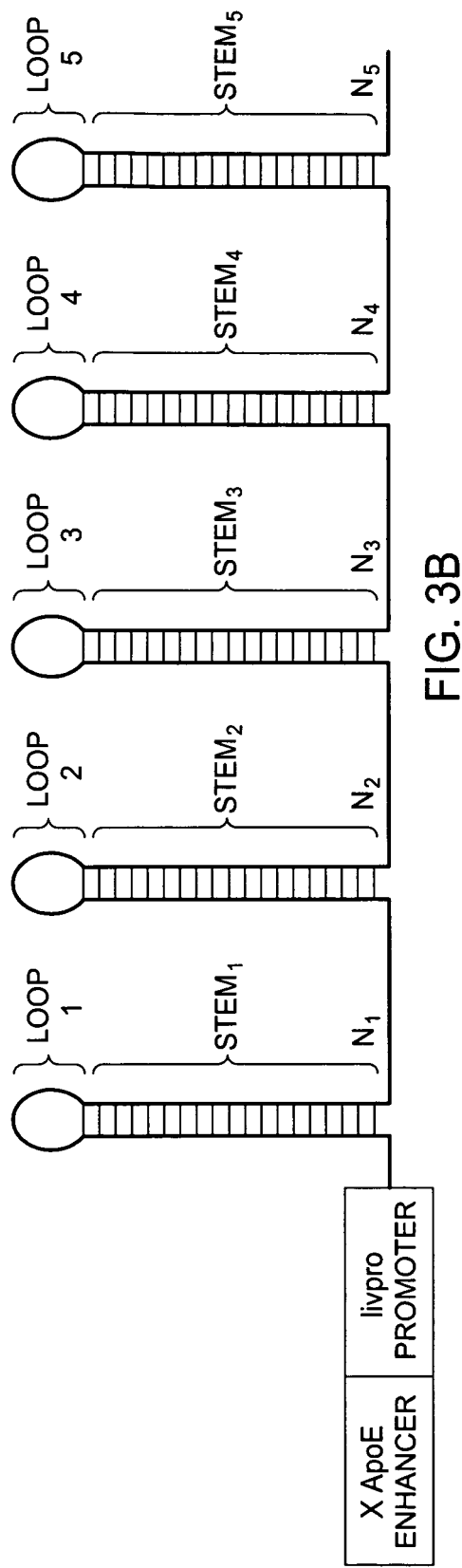

FIGS. 3A and 3B are simplified schematics of ApoE/livpro RNAi expression cassettes according to embodiments of the present invention where the ApoE/livpro RNAi expression cassette comprises one or more Apo E enhancers, one liver-specific promoter, and three distinct RNAi stem-loop structures (FIG. 3A) and five distinct RNAi stem-loop structures (FIG. 3B). It should be understood by those skilled in the art that ApoE/livpro RNAi expression cassettes of the present invention may contain two, four, six or more stem-loop structures and that the embodiments shown in this figure are merely exemplary. As discussed in the description of FIG. 2, the ApoE enhancer may comprise one or more ApoE enhancer sequences. The liver-specific promoter comprises the sequences necessary for transcription of the RNAi agents by Pol II and to afford liver specificity. In preferred embodiments, the stem regions (labeled here 1 through 5) comprise between about 17-25 base pairs, preferably 19 base pairs. The loop regions (also labeled 1 through 5) comprise between about 3-20 nucleotides, preferably about 5 to 9 nucleotides, and more preferably 6 nucleotides. The spacer regions ($N_1$, $N_2$ . . . ) between RNAi stems comprise about 4-10 nucleotides, preferably 6 nucleotides.

Figure 4A:
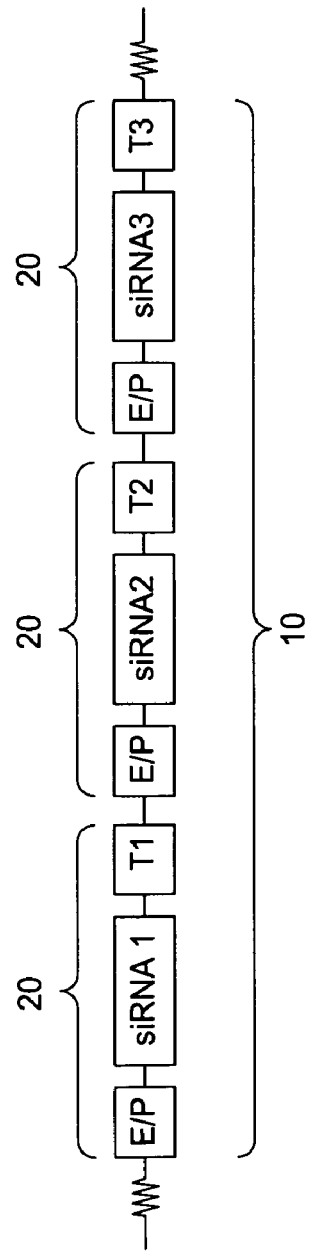
FIGS. 4A, 4B, 4C, and 4D are simplified schematic representations of embodiments of multiple-promoter ApoE/livpro RNAi expression cassettes according to the present invention where multiple RNAi agents are delivered simultaneously.
Figure 4B:
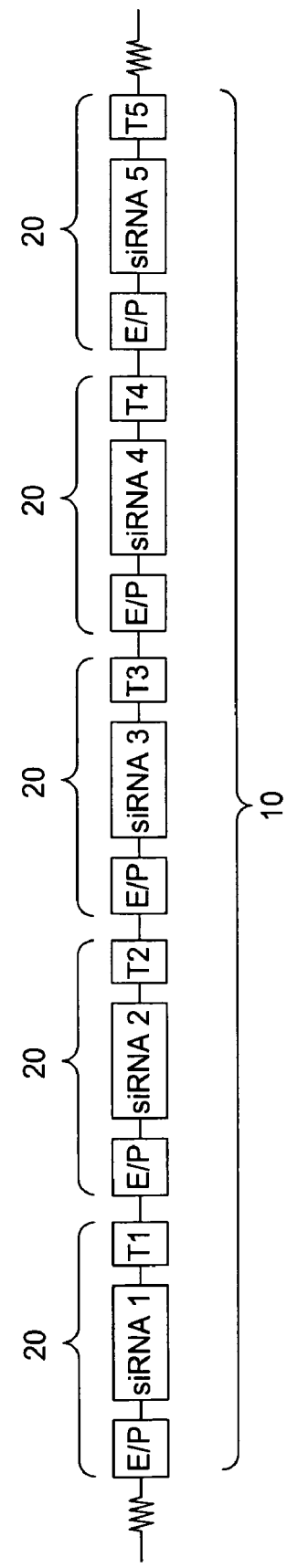

FIGS. 4A and 4B are schematics of exemplary multiple-promoter ApoE/livpro RNAi expression cassettes according to certain embodiments of the present invention. FIG. 4A shows an embodiment of a multiple-promoter expression cassette (10) with three [ApoE enhancer/livpro-RNAi agent-termination] components (shown at 20), and FIG. 4B shows an embodiment of a multiple-promoter expression cassette (10) with five [ApoE enhancer/livpro-RNAi agent-termination] components (shown at 20). E/P represents the ApoE enhancer/liver-specific promoter elements (that may comprise one or more than one ApoE enhancer sequence). RNAi1, RNAi2, RNAi3, RNAi4 and RNAi5 represent sequences for five different RNAi agents. T1, T2, T3, T4, and T5 represent termination elements. The multiple-promoter ApoE/livpro RNAi expression cassettes according to the present invention may contain two or more [ApoE enhancer/livpro-RNAi agent-termination] components where the number of [ApoE enhancer/livpro-RNAi agent-termination] components included in any multiple-promoter ApoE/livpro RNAi expression cassette is limited by, e.g., packaging size of the delivery system chosen (for example, some viruses, such as AAV, have relatively strict size limitations); cell toxicity, and maximum effectiveness (i.e. when, for example, expression of four RNAi sequences is as effective therapeutically as the expression of ten RNAi sequences).

The two or more RNAi agents in a multiple-RNAi agent ApoE/livpro RNAi expression cassette almost always have different sequences; that is RNAi1, RNAi2, RNAi3, RNAi4 and RNAi5 are all different from one another. The termination elements in any cassette may be the same (that is, e.g., the sequence of two or more of T1, T2, T3, T4 and T5 may be the same); all the termination elements within any cassette may be different from one another; or there may be a combination of termination elements represented only once and termination elements represented two times or more within any cassette, as long as whatever termination elements are selected work appropriately with the liver-specific promoter used and the Pol II enzyme. Termination elements useful in the present invention include the U1 termination sequence (U1 box), the synthetic polyA terminator, and the so-called minimal PolyA terminator. Transcriptional pause sites, such as MAZ1 and MAZ2, (see Ashfield et al EMBO J 1994 Vol13 No 23 5656 pp and Yonaha and Proudfoot EMBO J. 2000 Jul. 17; 19(14): 3770-7) may be inserted upstream of the polyA terminators to assist in coupling of transcription termination and polyadenylation.

Figure 4C:
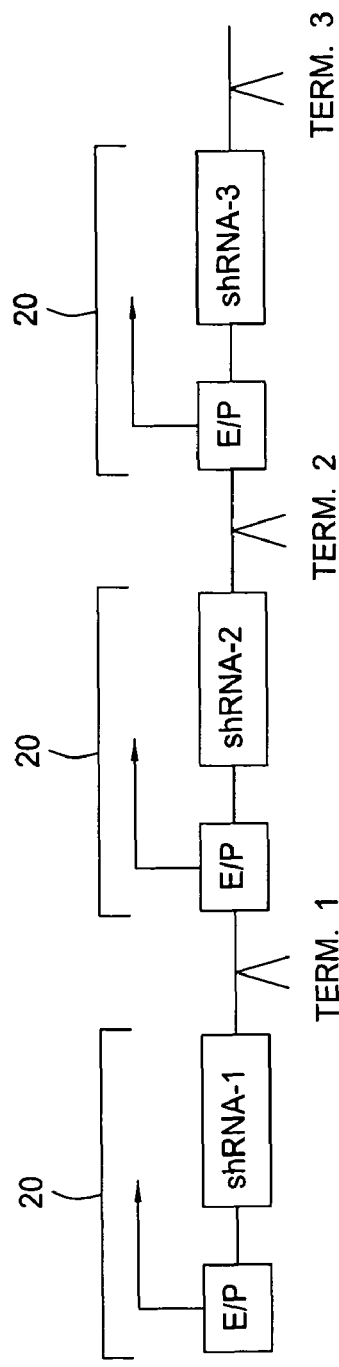
Figure 4D:
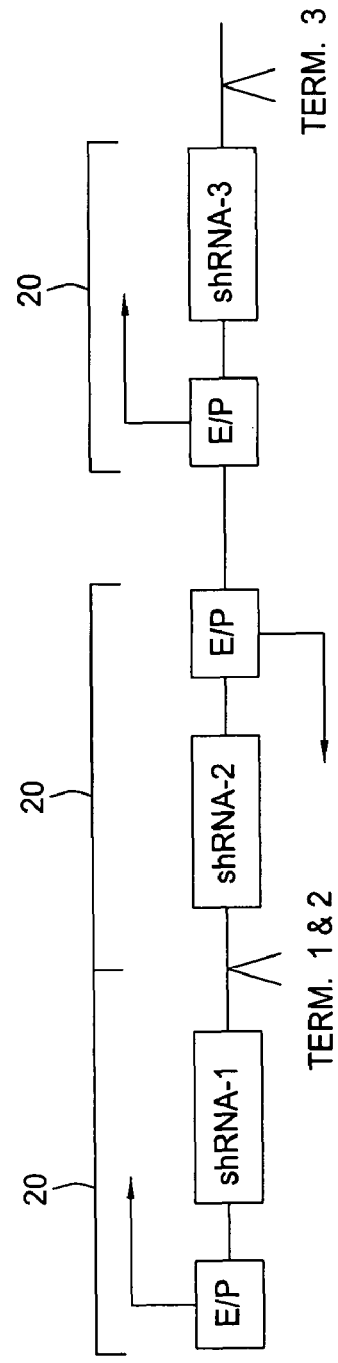

FIGS. 4C and 4D show exemplary multiple-promoter ApoE/livpro RNAi expression cassettes comprising embodiments of multiple-promoter ApoE/livpro RNAi expression cassettes that express short shRNAs. shRNAs are short duplexes where the sense and antisense strands are linked by a hairpin loop. Once expressed, shRNAs are processed into RNAi species by the enzyme Dicer. Again, E/P represents the ApoE enhancer/liver-specific promoter elements (that may comprise one or more than one ApoE enhancer sequence), and the arrows indicate the direction of transcription. Term1, Term2, and Term3 represent three termination sequences, and shRNA-1, shRNA-2 and shRNA-3 represent three different shRNA species. It should be noted that both embodiments shown in FIGS. 4C and 4D show ApoE/livpro RNAi expression cassettes with three shRNA agents; however, various embodiments of the present invention include one shRNA agent, two shRNA agents, four shRNA agents, and so on. FIG. 4C shows each of the three [ApoE enhancer/livpro-RNAi agent-termination] components (20) in the same orientation within the expression cassette, while FIG. 4D shows the [ApoE enhancer/livpro-RNAi agent-termination] components for shRNA-1 and shRNA-3 in one orientation, and the [ApoE enhancer/livpro-RNAi agent-termination] component for sh-RNA2 in the opposite orientation (i.e., transcription takes place on both strands of the cassette).

The RNAi sequences encoded by the ApoE/livpro RNAi expression cassettes of the present invention result in the expression of small interfering RNAs that are or are processed to short, double-stranded RNAs that are not toxic in normal mammalian cells. The RNAi sequences may be presented as short hairpin RNA substrates or as a part of a primary microRNA structure. If presented in the latter configuration, the effective RNAi molecule, aka the guide strand, is inserted into the primary microRNA sequence such that it replaces the original microRNA guide strand leaving the overall structure of the primary microRNA intact. There is no particular limitation in the length of the RNAi agents expressed by the ApoE/livpro RNAi expression cassettes of the present invention as long as they do not show cellular toxicity. The RNAi agents can be 17 to 25 bp in length, and are more preferably 19 bp in length. The double-stranded or stem portions of the RNAi agents may be completely homologous, or may contain non-paired portions due to sequence mismatch (the corresponding nucleotides on each strand are not complementary), bulges (lack of a corresponding complementary nucleotide on one strand), and the like. Such non-paired portions can be tolerated to the extent that they do not significantly interfere with RNAi duplex formation or efficacy. If expressed as a shRNA, the length of the single-stranded loop portion of the shRNA may be 3 to 25 nucleotides in length, and is preferably 5 to 9 nucleotides in length.

If there are multiple RNAi agents being delivered, the sequence of the stem structures of the two or more RNAi agents in the expression cassette of the present invention may be the same or different, but the sequences of the stems of the RNAi agents in each ApoE/livpro RNAi expression cassette are almost always different from one another. Also the length of the stems and the loops (if the agents are shRNA agents) of the different RNAi agents in the ApoE/livpro RNAi expression cassette may have the same length or a different length as the other stems and/or other loops of the other RNAi agents in the ApoE/livpro RNAi cassette. Also, in some embodiments—such as those shown in FIGS. 3A and 3B—the two or more stem-loop structures of the present invention are separated by spacer regions. The spacer regions comprise nucleotides, either naturally-occurring or synthetic. The length of the spacer regions between the stem-loop structures may be about 4 to 20 nucleotides, and is preferably about 6 nucleotides. The spacer regions between the RNAi agents in the expression cassettes of the present invention may have the same sequence or have different sequences and may be the same or a different length.

The nucleic acid sequences that are targets for the RNAi agents of the present invention include any viral genes, oncogenes, bacterial genes, developmental genes, and the like that are desired to be repressed specifically in the liver. Such liver-specific diseases include, but are not limited to, hepatitis A, B or C, Alagille syndrome, autoimmune hepatitis, biliary atresia, liver cancers (hepatocellular hyperplasia, hepatocellular adenomas, focal nodular hyperplasia, hepatocellular carcinomas), cirrhosis and primary biliary cirrhosis, cystic diseases (choledocal cysts, polycystic-disease, Caroli's syndrome, congenital hepatic fibrosis, fatty liver, galactosemia, primary sclerosing cholangitis, tyrosinemia, glycogen storage disease, and Wilson's disease, and the target nucleic acid sequences to be repressed are any nucleic acid sequences that, as a result of such repression in the liver, act in a therapeutic manner.

The sequences chosen for the RNAi agents are selected based upon the genetic sequence of the gene sequence(s) desired to be repressed; and preferably are based on regions of the gene sequences that are conserved. Methods of alignment of sequences for comparison and RNAi sequence selection are well known in the art. The determination of percent identity between two or more sequences can be accomplished using a mathematical algorithm. Preferred, non-limiting examples of such mathematical algorithms are the algorithm of Myers and Miller (1988); the search-for-similarity-method of Pearson and Lipman (1988); and that of Karlin and Altschul (1993). Preferably, computer implementations of these mathematical algorithms are utilized. Such implementations include, but are not limited to: CLUSTAL in the PC/Gene program (available from Intelligenetics, Mountain View, Calif.); the ALIGN program (Version 2.0), GAP, BESTFIT, BLAST, FASTA, Megalign (using Jotun Hein, Martinez, Needleman-Wunsch algorithms), DNAStar Lasergene (see www.dnastar.com) and TFASTA in the Wisconsin Genetics Software Package, Version 8 (available from Genetics Computer Group (GCG), 575 Science Drive, Madison, Wis., USA). Alignments using these programs can be performed using the default parameters or parameters selected by the operator. The CLUSTAL program is well described by Higgins. The ALIGN program is based on the algorithm of Myers and Miller; and the BLAST programs are based on the algorithm of Karlin and Altschul. Software for performing BLAST analyses is publicly available through the National Center for Biotechnology Information (http://www.ncbi.nlm.nih.gov/).

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Typically, inhibition of target sequences by RNAi requires a high degree of sequence homology between the target sequence and the sense strand of the RNAi molecules. In some embodiments, such homology is higher than about 70%, and may be higher than about 75%. Preferably, homology is higher than about 80%, and is higher than 85% or even 90%. More preferably, sequence homology between the target sequence and the sense strand of the RNAi is higher than about 90%, 91%, 92%, 93%, 94%, 95%, 96%, 97%, 98% or 99%.

In embodiments where the ApoE/livpro RNAi expression construct is used to target viral infections such as hepatits A, B or C, it may be that sequence homology between the genomes of the various subspecies of the virus, even in conserved regions, does not reach the level of over 90% or even 80% over 15 to 30 consecutive nucleotides. In such a case, sequence homology between the target sequence for some subspecies and the sense strand of the RNAi may be 80% or less. On the other hand, the ApoE/livpro RNAi expression construct embodiments of the present invention are particularly useful when targeting genes that do not display high sequence homology across individuals as each ddRNAi agent in a multiple-RNAi agent ApoE/livpro RNAI expression cassette can be used to address varying allelic sequences.

When addressing hepatitis, a major problem of current anti-viral therapies is the emergence of resistant variants, known generally as escape mutants (Gitlin et. al. *J. of Virol.* 79; 1027-1035, 2005). One aspect of the present invention neutralizes emergent escape mutants. In some embodiments of this invention the selection of multiple RNAi sequences to treat viral infections are chosen based on the emergence of escape mutants from treatment of infected cells single sequence of RNAi. Emergent escape mutants are determined by treatment with an expression construct containing a single sequence of RNAi after the cells have been infected with virus. Cells containing resistant viruses that emerge are harvested and the viral genomes sequenced. Sequencing reveals predominant mutations that arise to resist viral inhibition. An ApoE/livpro RNAi expression construct of the present invention may be generated that contains multiple RNAi sequences where the sequences are based upon the genetic sequence of the target gene and additionally sequences of the point mutations that arise to resist RNAi treatment.

In addition to selecting the RNAi sequences based on conserved regions of a gene, selection of the RNAi sequences may be based on other factors. Despite a number of attempts to devise selection criteria for identifying sequences that will be effective in RNAi based on features of the desired target sequence (e.g., percent GC content, position from the translation start codon, or sequence similarities based on an in silico sequence database search for homologs of the proposed RNAi, thermodynamic pairing criteria), it is presently not possible to predict with much degree of confidence which of the myriad possible candidate RNAi sequences that correspond to a gene, in fact, elicit an optimal RNA silencing response. Instead, individual specific candidate RNAi polynucleotide sequences typically are generated and tested to determine whether interference with expression of a desired target can be elicited.

The ApoE/livpro RNAi expression cassettes may be configured where multiple cloning sites and/or unique restriction sites are located strategically, such that the ApoE enhancer, liver-specific promoter, ddRNAi agents and termination elements are easily removed or replaced. The ApoE/livpro RNAi expression cassettes may be assembled from smaller oligonucleotide components using strategically located restriction sites and/or complementary sticky ends. The base vector for one approach according to embodiments of the present invention consists of plasmids with a multilinker in which all sites are unique (though this is not an absolute requirement).

The ApoE/livpro RNAi expression constructs may contain additional genetic elements. The types of elements that may be included in the constructs are not limited in any way and may be chosen by one with skill in the art. For example, additional genetic elements may include a reporter gene, such as one or more genes for a fluorescent marker protein such as GFP or RFP; an easily assayed enzyme such as beta-galactosidase, luciferase, beta-glucuronidase, chloramphenical acetyl transferase or secreted embryonic alkaline phosphatase; or proteins for which immunoassays are readily available such as hormones or cytokines. Other genetic elements that may find use in embodiments of the present invention include those coding for proteins which confer a selective growth advantage on cells such as adenosine deaminase, aminoglycodic phosphotransferase, dihydrofolate reductase, hygromycin-B-phosphotransferase, drug resistance, or those genes coding for proteins that provide a biosynthetic capability missing from an auxotroph. If a reporter gene is included in the ApoE/livpro RNAi expression construct, an internal ribosomal entry site (IRES) sequence can be included. Preferably, the additional genetic elements are operably linked with and controlled by an independent promoter/enhancer. In addition a suitable origin of replication for propagation of the construct in bacteria may be employed. The sequence of the origin of replication generally is separated from the ApoE/livpro RNAi expression cassette and other genetic sequences that are to be expressed in the liver. Such origins of replication are known in the art and include the pUC, ColE1, 2-micron or SV40 origins of replication.

A viral delivery system based on any appropriate virus may be used to deliver the ApoE/livpro RNAi expression constructs of the present invention. In addition, hybrid viral systems may be of use. The choice of viral delivery system will depend on various parameters, such as efficiency of delivery into the liver, transduction efficiency of the system, pathogenicity, immunological and toxicity concerns, and the like. It is clear that there is no single viral system that is suitable for all applications. When selecting a viral delivery system to use in the present invention, it is important to choose a system where ApoE/livpro RNAi expression construct-containing viral particles are preferably: 1) reproducibly and stably propagated; 2) able to be purified to high titers; and 3) able to mediate targeted delivery (delivery of the ApoE/livpro RNAi expression construct to the liver without widespread dissemination).

In general, the five most commonly used classes of viral systems used in gene therapy can be categorized into two groups according to whether their genomes integrate into host cellular chromatin (oncoretroviruses and lentiviruses) or persist in the cell nucleus predominantly as extrachromosomal episomes (adeno-associated virus, adenoviruses and herpesviruses). Integrating vectors are the tools of choice if stable genetic alteration needs to be maintained in actively dividing cells.

For example, in one embodiment of the present invention, viruses from the Parvoviridae family are utilized. The Parvoviridae is a family of small single-stranded, non-enveloped DNA viruses with genomes approximately 5000 nucleotides long. Included among the family members is adeno-associated virus (AAV), a dependent parvovirus that by definition requires co-infection with another virus (typically an adenovirus or herpesvirus) to initiate and sustain a productive infectious cycle. In the absence of such a helper virus, AAV is still competent to infect or transducer a target cell by receptor-mediated binding and internalization, penetrating the nucleus in both non-dividing and dividing cells.

Once in the nucleus, the virus uncoats and the transgene is expressed from a number of different forms—the most persistent of which are circular monomers. AAV will integrate into the genome of 1-5% of cells that are stably transduced (Nakai, et al., *J. Virol.* 76:11343-349 (2002). Expression of the transgene can be exceptionally stable and in one study with AAV delivery of Factor IX, a dog model continues to express therapeutic levels of the protein over 5.0 years after a single direct infusion with the virus. Because progeny virus is not produced from AAV infection in the absence of helper virus, the extent of transduction is restricted only to the initial cells that are infected with the virus. It is this feature which makes AAV a preferred gene therapy vector for the present invention. Furthermore, unlike retrovirus, adenovirus, and herpes simplex virus, AAV appears to lack human pathogenicity and toxicity (Kay, et al., *Nature.* 424: 251 (2003) and Thomas, et al., *Nature Reviews, Genetics* 4:346-58 (2003)).

Typically, the genome of AAV contains only two genes. The "rep" gene codes for at least four separate proteins utilized in DNA replication. The "cap" gene product is spliced differentially to generate the three proteins that comprise the capsid of the virus. When packaging the genome into nascent virus, only the Inverted Terminal Repeats (ITRS) are obligate sequences; rep and cap can be deleted from the genome and be replaced with heterologous sequences of choice. However, in order produce the proteins needed to replicate and package the AAV-based heterologous construct into nascent virion, the rep and cap proteins must be provided in trans. The helper functions normally provided by co-infection with the helper virus, such as adenovirus or herpesvirus mentioned above also can be provided in trans in the form of one or more DNA expression plasmids. Since the genome normally encodes only two genes it is not surprising that, as a delivery vehicle, AAV is limited by a packaging capacity of 4.5 single stranded kilobases (kb). However, although this size restriction may limit the genes that can be delivered for replacement gene therapies, it does not adversely affect the packaging and expression of shorter sequences such as RNAi.

The utility of AAV for RNAi applications was demonstrated in experiments where AAV was used to deliver shRNA in vitro to inhibit p53 and Caspase 8 expression (Tomar et al., *Oncogene.* 22: 5712-15 (2003)). Following cloning of the appropriate sequences into a gutted AAV-2 vector, infectious AAV virions were generated in HEK293 cells and used to infect HeLa S3 cells. A dose-dependent decrease of endogenous Caspase 8 and p53 levels was demonstrated. Boden et al. also used AAV to deliver shRNA in vitro to inhibit HIV replication in tissue culture systems (Boden, et al., *J. Virol.* 77(21): 115231-35 (2003)) as assessed by p24 production in the spent media.

However, technical hurdles must be addressed when using AAV as a vehicle for ApoE/livpro RNAi expression constructs. For example, various percentages of the human population may possess neutralizing antibodies against certain AAV serotypes. However, since there are several AAV serotypes, for some of which the percentage of individuals harboring neutralizing antibodies is vastly reduced, other serotypes can be used or pseudo-typing may be employed. There are at least eight different serotypes that have been characterized, with dozens of others which have been isolated but have been less well described. Another limitation is that as a result of a possible immune response to AAV, AAV-based therapy may only be administered once; however, use of alternate, non-human derived serotypes may allow for repeat administrations. Administration route, serotype, and composition of the delivered genome all influence tissue specificity.

Another limitation in using unmodified AAV systems with the ApoE/livpro RNAi expression constructs is that transduction can be inefficient. Stable transduction in vivo may be limited to 5-10% of cells. However, different methods are known in the art to boost stable transduction levels. One approach is utilizing pseudotyping, where AAV-2 genomes are packaged using cap proteins derived from other serotypes. For example, by substituting the AAV-5 cap gene for its AAV-2 counterpart, Mingozzi et al. increased stable transduction to approximately 15% of hepatocytes (Mingozzi, et al., *J. Virol.* 76(20): 10497-502 (2002)). Thomas et al., transduced over 30% of mouse hepatocytes in vivo using the AAV8 capsid gene (Thomas, et al., J Virol. 2004 March; 78(6):3110-22.). Grimm et al. (*Blood.* 2003-02-0495) exhaustively pseudotyped AAV-2 with AAV-1, AAV-3B, AAV-4, AAV-5, and AAV-6 for tissue culture studies. The highest levels of transgene expression were induced by virion which had been pseudotyped with AAV-6; producing nearly 2000% higher transgene expression than AAV-2. Thus, the present invention contemplates use of a pseudotyped AAV virus to achieve high transduction levels, with a corresponding increase in the expression of the ApoE/livpro RNAi expression constructs.

Self complementary AAV vectors may also be used according to embodiments of the invention. The most significant distinction between a standard AAV vector and a self complementary vector is in the form of its genome and the size packaged. A standard AAV vector has 4.6 Kb of single stranded DNA while a self complementary AAV vector has 2.3 Kb of double stranded DNA. An AAV vector can be converted into a self complementary vector by introducing a mutation/deletion in one of the inverted terminal repeats (ITR). Each AAV genome has two such repeats at the 5' and 3' ends. Replication typically starts at one of the ITRs and commences through the genome and resolves at the other ITR. It is for this reason that AAV vectors contain genomes that are either positive or negative stranded. The sequences that govern transcriptional resolution most definitively are the D-sequence and the terminal resolution site (trs). These sequences sit between nucleotides 122-144 of the AAV2 genome (Wang et al (2003) Gene Therapy 10: 2106-2111) and deletion of them disallows transcriptional resolution at an ITR. It should be noted that, since the ITRs of AAV vectors are nearly identical, deletion of the D-sequence and trs can be done in either of the two ITRs. As a result of the ITR D-sequence and trs deletion, an elongating replication complex can no longer resolve, and the complex continues in an orientation opposite to the original direction, i.e. if the replication complex first generated a positive strand, it fails to resolve at the deleted ITR and then generates a negative strand that is complementary to the positive strand. This then results in a self complementary double stranded DNA molecule that will get packaged in the AAV vector provided its length is not over 2.3 kb and is preferably shorter. It should be noted that since ITRs of an AAV vector recombine during the replication process, a revertant phenotype, i.e. both ITRs regaining wild type sequences, may result. In order to alleviate this problem, ITRs of different AAV vectors must be used. For instance an AAV2 Left ITR with an AAV4 deleted Right ITR, etc. The sole criterion that governs the choice of ITRs to be combined lies in the sequence identity between the ITRs of the serotype. The ITRs of serotypes 2 and 5 are nearly identical, and the ITRs of serotypes 2 and 4 have an 81.6% similarity. After deletion of the D sequence and trs, the sequence identity between the ITRs of AAV 2 and AAV 4 drops to just over 50%. The combination of these two ITRs therefore generates a good combination of divergent ITRs and will result in a self complementary AAV vector that can no longer regenerate progeny with wildtype ITRs.

Self complementary vectors have considerable advantages over single stranded vectors in terms of their ability to effectively transduce cells. Pseudotyped with the capsid proteins of AAV8, it has been shown that AAV vectors can transduce upwards of 95% of targeted liver cells (see Nakai et al J Virol. 2005 January; 79(1):214-24 and Grimm et al, J Virol. 2006 January; 80(1):426-39).

Another viral delivery system useful with the ApoE/livpro RNAi expression constructs of the present invention is a system based on viruses from the family Retroviridae. Retroviruses comprise single-stranded RNA animal viruses that are characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus can then integrate into the host genome and be passed from parent cell to progeny cells as a stably-integrated component of the host genome.

In some embodiments, lentiviruses are the preferred members of the retrovirus family for use in the present invention. Lentivirus vectors are often pseudotyped with vesicular stomatitis virus glycoprotein (VSV-G), and have been derived from the human immunodeficiency virus (HIV), the etiologic agent of the human acquired immunodeficiency syndrome (AIDS); visna-maedi, which causes encephalitis (visna) or pneumonia in sheep; equine infectious anemia virus (EIAV), which causes autoimmune hemolytic anemia and encephalopathy in horses; feline immunodeficiency virus (FIV), which causes immune deficiency in cats; bovine immunodeficiency virus (BIV) which causes lymphadenopathy and lymphocytosis in cattle; and simian immunodeficiency virus (SIV), which causes immune deficiency and encephalopathy in non-human primates. Vectors that are based on HIV generally retain <5% of the parental genome, and <25% of the genome is incorporated into packaging constructs, which minimizes the possibility of the generation of reverting replication-competent HIV. Biosafety has been further increased by the development of self-inactivating vectors that contain deletions of the regulatory elements in the downstream long-terminal-repeat sequence, eliminating transcription of the packaging signal that is required for vector mobilization.

Reverse transcription of the retroviral RNA genome occurs in the cytoplasm. Unlike C-type retroviruses, the lentiviral cDNA complexed with other viral factors—known as the pre-initiation complex—is able to translocate across the nuclear membrane and transduce non-dividing cells. A structural feature of the viral cDNA—a DNA flap—seems to contribute to efficient nuclear import. This flap is dependent on the integrity of a central polypurine tract (cPPT) that is located in the viral polymerase gene, so most lentiviral-derived vectors retain this sequence. Lentiviruses have broad tropism, low inflammatory potential, and result in an integrated vector. The main limitations are that integration might induce oncogenesis in some applications. The main advantage to the use of lentiviral vectors is that gene transfer is persistent in most tissues or cell types.

A lentiviral-based construct used to express the ddRNAi agents preferably comprises sequences from the 5' and 3' LTRs of a lentivirus. More preferably the viral construct comprises an inactivated or self-inactivating 3' LTR from a lentivirus. The 3' LTR may be made self-inactivating by any method known in the art. In a preferred embodiment, the U3 element of the 3' LTR contains a deletion of its enhancer sequence, preferably the TATA box, Sp1 and NF-kappa B sites. As a result of the self-inactivating 3' LTR, the provirus that is integrated into the host cell genome will comprise an inactivated 5' LTR. The LTR sequences may be LTR sequences from any lentivirus from any species. The lentiviral-based construct also may incorporate sequences for MMLV or MSCV, RSV or mammalian genes. In addition, the U3 sequence from the lentiviral 5' LTR may be replaced with a promoter sequence in the viral construct. This may increase the titer of virus recovered from the packaging cell line. An enhancer sequence may also be included.

Other viral or non-viral systems known to those skilled in the art may be used to deliver the ApoE/livpro RNAi expression cassettes of the present invention to the liver, including but not limited to gene-deleted adenovirus-transposon vectors that stably maintain virus-encoded transgenes in vivo through integration into host cells (see Yant, et al., Nature Biotech. 20:999-1004 (2002)); systems derived from Sindbis virus or Semliki forest virus (see Perri, et al, J. Virol. 74(20): 9802-07 (2002)); systems derived from Newcastle disease virus or Sendai virus; or mini-circle DNA vectors devoid of bacterial DNA sequences (see Chen, et al., Molecular Therapy. 8(3):495-500 (2003)). Mini-circle DNA as described in U.S. Patent Publication No. 2004/0214329 discloses vectors that provide for persistently high levels of nucleic acid transcription. The circular vectors are characterized by being devoid of expression-silencing bacterial sequences, and may include a unidirectional site-specific recombination product sequence in addition to an expression cassette.

In addition, hybrid viral systems may be used to combine useful properties of two or more viral systems. For example, the site-specific integration machinery of wild-type AAV may be coupled with the efficient internalization and nuclear targeting properties of adenovirus. AAV in the presence of adenovirus or herpesvirus undergoes a productive replication cycle; however, in the absence of helper functions, the AAV genome integrates into a specific site on chromosome 19. Integration of the AAV genome requires expression of the AAV rep protein. As conventional rAAV vectors are deleted for all viral genes including rep, they are not able to specifically integrate into chromosome 19. However, this feature may be exploited in an appropriate hybrid system. In addition, non-viral genetic elements may be used to achieve desired properties in a viral delivery system, such as genetic elements that allow for site-specific recombination.

Figure 5A:
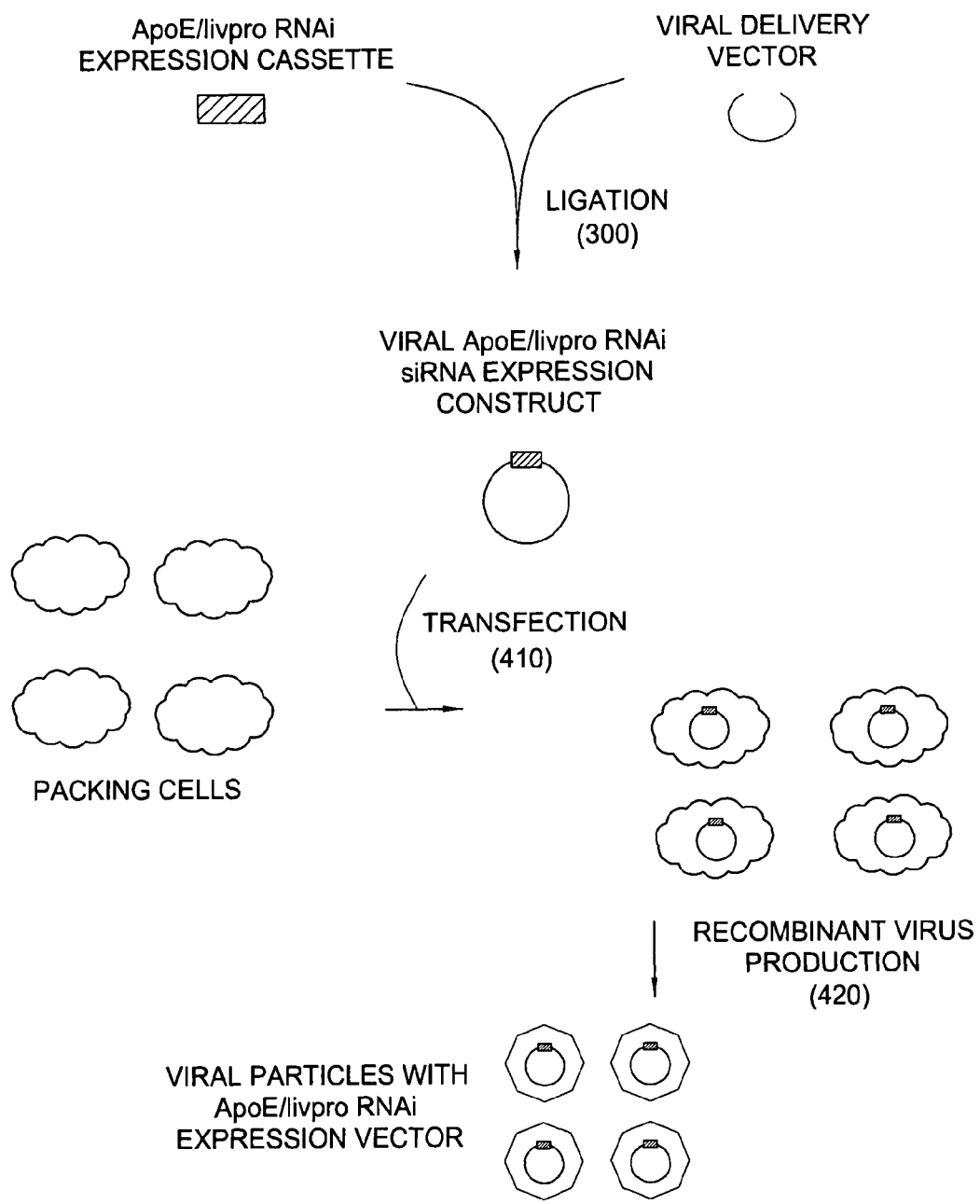
FIGS. 5A and 5B show alternative methods for producing viral particles for delivery of constructs comprising the ApoE/livpro RNAi expression cassettes to the liver.
Figure 5B:
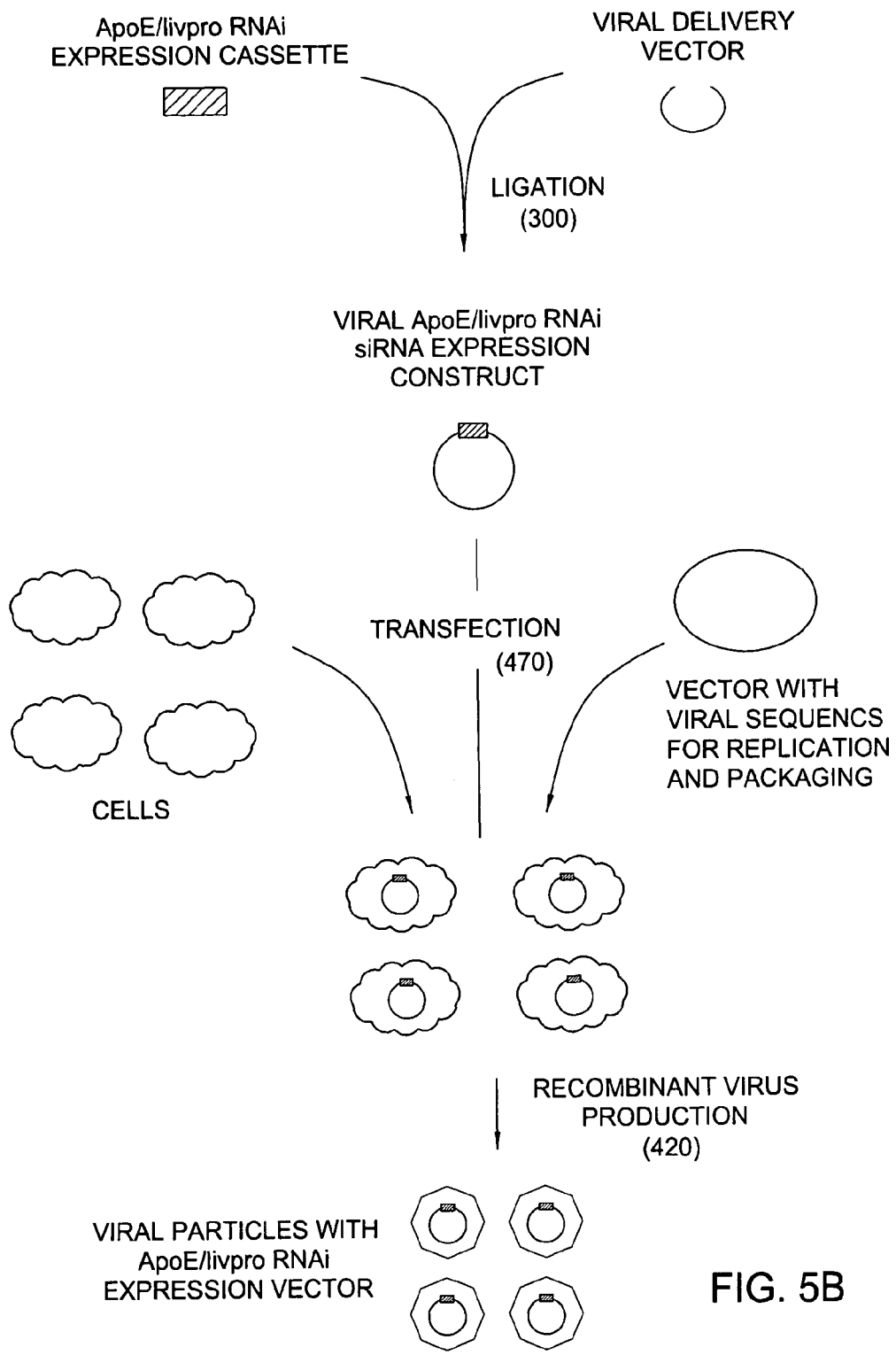

Step 400 of FIG. 1 recites that the ApoE/livpro RNAi expression construct is packaged into viral particles. Any method known in the art may be used to produce infectious viral particles whose genome comprises a copy of the viral ApoE/livpro RNAi expression construct. FIGS. 5A and 5B show alternative methods for packaging the ApoE/livpro RNAi expression constructs of the present invention into viral particles for delivery. The method in FIG. 5A utilizes packaging cells that stably express in trans the viral proteins that are required for the incorporation of the viral ApoE/livpro RNAi expression construct into viral particles, as well as other sequences necessary or preferred for a particular viral delivery system (for example, sequences needed for replication, structural proteins and viral assembly) and either viral-derived or artificial ligands for tissue entry. In FIG. 5A, a ApoE/livpro RNAi expression cassette is ligated to a viral delivery vector (step 300), and the resulting viral ApoE/livpro RNAi expression construct is used to transfect packaging cells (step 410). The packaging cells then replicate viral sequences, express viral proteins and package the viral ApoE/livpro RNAi expression constructs into infectious viral particles (step 420). The packaging cell line may be any cell line that is capable of expressing viral proteins, including but not limited to 293, HeLa, A549, PerC6, D17, MDCK, BHK, bing cherry, phoenix, Cf2Th, or any other line known to or developed by those skilled in the art. One packaging cell line is described, for example, in U.S. Pat. No. 6,218,181.

Alternatively, a cell line that does not stably express necessary viral proteins may be co-transfected with two or more constructs to achieve efficient production of functional particles. One of the constructs comprises the viral ApoE/livpro RNAi expression construct, and the other plasmid(s) comprises nucleic acids encoding the proteins necessary to allow the cells to produce functional virus (replication and packaging construct) as well as other helper functions. The method shown in FIG. 5B utilizes cells for packaging that do not stably express viral replication and packaging genes. In this case, the ApoE/livpro RNAi expression construct is ligated to the viral delivery vector (step 300) and then co-transfected with one or more vectors that express the viral sequences necessary for replication and production of infectious viral particles (step 430). The cells replicate viral sequences, express viral proteins and package the viral RNAi expression constructs into infectious viral particles (step 420).

The packaging cell line or replication and packaging construct may not express envelope gene products. In these embodiments, the gene encoding the envelope gene can be provided on a separate construct that is co-transfected with the viral ApoE/livpro RNAi expression construct. As the envelope protein is responsible, in part, for the host range of the viral particles, the viruses may be pseudotyped. As described supra, a "pseudotyped" virus is a viral particle having an envelope protein that is from a virus other than the virus from which the genome is derived. One with skill in the art can choose an appropriate pseudotype for the viral delivery system used and cell to be targeted. In addition to conferring a specific host range, a chosen pseudotype may permit the virus to be concentrated to a very high titer. Viruses alternatively can be pseudotyped with ecotropic envelope proteins that limit infection to a specific species (e.g., ecotropic envelopes allow infection of, e.g., murine cells only, where amphotropic envelopes allow infection of, e.g., both human and murine cells.) In addition, genetically-modified ligands can be used for cell-specific targeting, such as the asialoglycoprotein for hepatocytes, or transferrin for receptor-mediated binding.

After production in a packaging cell line, the viral particles containing the ApoE/livpro RNAi expression cassettes are purified and quantified (titered). Purification strategies include density gradient centrifugation, or preferably, column chromatographic methods.

In step 500 of FIG. 1, the ApoE/livpro RNAi expression construct is delivered to the liver. The ApoE/livpro RNAi expression construct of the present invention may be introduced into the cells in vitro or ex vivo and then subsequently placed into an animal to affect therapy, or administered directly to an individual by in vivo administration. Delivery by viral infection is a preferred method of delivery; however, any appropriate method of delivery of the ApoE/livpro RNAi expression construct may be employed. The vectors comprising the cassettes can be administered to a mammalian host using any convenient protocol, where a number of different such protocols are known in the art.

A variety of techniques are available and well known for delivery of nucleic acids into cells, for example liposome- or micelle-mediated transfection or transformation, transformation of cells with attenuated virus particles or bacterial cells, cell mating, transformation or transfection procedures known to those skilled in the art or microinjection.

The most common transfection reagents are charged lipophilic compounds that are capable of crossing cell membranes. When these are complexed with a nucleic acid they can act to carry DNA across the cell membrane. A large number of such compounds are available commercially. Polyethylenimine (PEI) is a new class of transfection reagents, chemically distinct from the lipophilic compounds that act in a similar fashion, but have the advantage they can also cross nuclear membranes. An example of such a reagent is ExGen 500 (Fermentas). A construct or synthetic gene according to the present invention may be packaged as a linear fragment within a synthetic liposome or micelle for delivery into the target cell.

Alternatively, ddRNAi expression constructs containing the ApoE/livpro RNAi expression cassette may be introduced into the liver by other routes, including microinjection or fusion of vesicles. The nucleic acids may be coated onto gold microparticles, and delivered intradermally by a particle bombardment device, or "gene gun" as described in the literature (see, for example, Tang et al., Nature. 356:152-154 (1992)), where gold microprojectiles are coated with the DNA, then bombarded into the liver.

Another delivery method useful for the ApoE/livpro RNAi expression constructs according to the present invention comprises the use of Cyclosert™ technology as described in U.S. Pat. No. 6,509,323 to Davis et. al. Cyclosert™ technology platform is based upon cup-shaped cyclic repeating molecules of glucose known as cyclodextrins. The "cup" of the cyclodextrin molecule can form "inclusion complexes" with other molecules, making it possible to combine the Cyclosert™ polymers with other moieties to enhance stability or to add targeting ligands. In addition, cyclodextrins have generally been found to be safe in humans (individual cyclodextrins currently enhance solubility in FDA-approved oral and IV drugs) and can be purchased in pharmaceutical grade on a large scale at low cost. These polymers are extremely water soluble, non-toxic and non-immunogenic at therapeutic doses, even when administered repeatedly. The polymers can easily be adapted to carry a wide range of small-molecule therapeutics at drug loadings that can be significantly higher than liposomes.

The vectors comprising the ApoE/livpro RNAi expression cassettes of the present invention can be formulated into preparations for injection or administration by dissolving, suspending or emulsifying them in an aqueous or nonaqueous solvent, such as oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In addition, the vectors comprising the ApoE/livpro RNAi expression cassettes of the present invention can be formulated into pharmaceutical compositions by combination with appropriate, pharmaceutically acceptable carriers or diluents. In pharmaceutical dosage forms, the vectors comprising the ApoE/livpro RNAi cassettes may be administered alone or in association or combination with other pharmaceutically active compounds.

EXAMPLES

Example 1

Selection of HCV Target Sequences

Selection of RNAs useful as a therapeutic against diseases or disorders is not a straight-forward proposition. In addition to the problem of the generation of escape mutants in treating viral infections, the high mutation rate of both viral and cancerous genes leads to a rather large degree of sequence divergence within a population of affected individuals. For example, individuals infected with hepatitis virus may harbor virus with genotypes differing by as much as 31-34% in their nucleotide sequences, and subtypes (species within a given genotype) may differ by 20-23% based on full-length genomic sequence comparisons. Thus, in the case of HCV, regions of the viral genome with a high degree of conservation are identified and chosen to ensure the broadest therapeutic applicability. To select candidate sequences, an alignment of all published independent full-length or near-full-length sequences may be performed. When the sequence analyses are concluded, a list of candidate RNAi sequences is generated. In order to rank the sequences on the basis of relative potency, the ability of individual pre-synthesized RNAi agents to inhibit the activity of a target gene is tested. The same approach is used when targeting oncogenes, developmental genes and the like.

To select candidate sequences for target by ApoE/livpro RNAi cassettes of the present invention, an alignment of all published independent full-length or near-full-length HCV sequences was performed; currently there are over 200 such sequences available representing all genotypes. Several candidate regions for selection and development of RNAi therapeutics currently exist and it is well-documented that the 5' and 3'UTR regions are amongst the most highly conserved regions in the HCV genome. Despite perception that these non-coding sequences may not represent optimal sequences to target due to the potential for steric hindrance with the cellular translation complex proteins or regulatory proteins, Yokota et al. have already identified a highly functional RNAi targeting the 5' UTR in a replicon system (*EMBO Rep.* 4(6): 602-608 (2003)). Although it would be beneficial to identify several regions of absolute identity-within individual stretches of 21 nucleotides (the corresponding size of the targeting sequences in a shRNA species), analysis to date demonstrates that such a degree of conservation does not occur within the various subtypes of a specified genotype, let alone across all genotypes. Thus, selection may include segments of the genome in which greater than 80% of the regions maintain absolute conservation. The expression of three independent shRNAs compensates for the sequence variability, allowing for a combination therapy contained within a single delivery vehicle.

Alternatively, if conserved regions that meet the selection criterion in an analysis of all HCV genotypes are not identified, which was the case with HCV, sequence analysis may be restricted to genotype 1 (1a and 1b), which accounts for nearly three quarters of the infected population with the United States and, with the exception of Africa, is the predominate genotype throughout the world. In addition, the most current effective anti-HCV therapy, a combination of pegylated interferon with Ribavirin (a guanosine analogue), is rather inefficient against genotype 1, but highly efficient against the other genotypes. Thus, the greatest need for an alternative therapy exists in the largest patient population. As sequence alignments only reveal homology, other selection criteria, such as relative GC content and the lack of cross specificity when queried against sequence databases, is applied when selecting the final RNAi agents to be tested.

For example, for one experiment, alignment was performed for multiple sequences from HCV subtypes 1*a* and 1*b*. A few conserved regions were identified as being long enough from which to select RNAi agents for testing (>19 nucleotides). The 5'NTR and 3'NTR regions were the most conserved regions. Since the regions of homology that were identified were quite long, alignment also was performed between different genotypes. Combining the two alignments allowed selection of universally conserved regions. Some regions, such as long stretches of A's or U's, or of G's and C's were removed from consideration, leaving "qualified" regions for further selection. Only one universally conserved region was identified in the whole coding region (the open reading frame) for all of the genotypes of HCV considered; therefore, the sequences selected for targets in most cases were those that are conserved in subtypes 1*a* and 1*b*.

Once "qualified" regions were identified, individual RNAi sequences were selected applying the criterion that the 5' end of the antisense strand in the RNAi agent should possess a lower free energy than the 3' end. "Neighbor pair free energy" rules were applied to calculate free energy for the terminal five nucleotides on both the 5' and 3' ends of all potential RNAi agents selected thus far. As a result, a total of 56 potential RNAi agents were identified: thirty in the 5'NTR (5'-n), twelve in the ORF (c-n), and fourteen in the 3'NTR (3'-n) (see Table 1).

TABLE 1

RNAi Sequences

| RNAi agent | Sequence | SEQ ID NO. | Luc-HCV Reporter Plasmid |
|---|---|---|---|
| 5'-1 | gCTGTGAGGAACTACTGTCT | SEQ ID NO. 1 | 20 |
| 5'-2 | GTCTAGCCATGGCGTTAGT | SEQ ID NO. 2 | — |
| 5'-3 | GGAGAGCCATAGTGGTCTG | SEQ ID NO. 3 | 16, 20 |
| 5'-4 | GCGGAACCGGTGAGTACAC | SEQ ID NO. 4 | 16 |
| 5'-5 | GTCTGCGGAACCGGTGAGTA | SEQ ID NO. 5 | 16 |
| 5'-6 | GCGAAAGGCCTTGTGGTACT | SEQ ID NO. 6 | 16, 17 |
| 5'-7 | GATAGGGTGCTTGCGAGTG | SEQ ID NO. 7 | 16 |
| 5'-8 | GAGGTCTCGTAGACCGTGCA | SEQ ID NO. 8 | 16, 17 |
| 5'-9 | gCTTGTGGTACTGCCTGATA | SEQ ID NO. 9 | — |
| 5'-10 | gCTGCCTGATAGGGTGCTTG | SEQ ID NO. 10 | 17 |
| 5'-11 | ATCACTCCCCTGTGAGGAA | SEQ ID NO. 11 | — |
| 5'-12 | ACTCCCTGTGAGGAACTA | SEQ ID NO. 12 | — |
| 5'-13 | CGTCTAGCCATGGCGTTAG | SEQ ID NO. 13 | — |
| 5'-14 | TCTAGCCATGGCGTTAGTA | SEQ ID NO. 14 | — |
| 5'-15 | CTAGCCATGGCGTTAGTAT | SEQ ID NO. 15 | — |
| 5'-16 | TGTCGTACAGCCTCCAGGC | SEQ ID NO. 16 | — |
| 5'-17 | CCGGGAGAGCCATAGTGGT | SEQ ID NO. 17 | — |
| 5'-18 | AGAGCCATAGTGGTCTGCG | SEQ ID NO. 18 | — |
| 5'-19 | GCCATAGTGGTCTGCGGAA | SEQ ID NO. 19 | — |
| 5'-20 | CCGGTGAGTACACCGGAAT | SEQ ID NO. 20 | — |
| 5'-21 | CGGTGAGTACACCGGAATC | SEQ ID NO. 21 | — |
| 5'-22 | GACTGGGTCCTTTCTTGGA | SEQ ID NO. 22 | — |
| 5'-23 | GACCGGGTCCTTTCTTGGA | SEQ ID NO. 23 | — |
| 5'-24 | ACCGGGTCCTTTCTTGGAA | SEQ ID NO. 24 | — |
| 5'-25 | TGGGTTGCGAAAGGCCTTG | SEQ ID NO. 25 | — |
| 5'-26 | TTGCGAAAGGCCTTGTGGT | SEQ ID NO. 26 | — |
| 5'-27 | AGGCCTTGTGGTACTGCCT | SEQ ID NO. 27 | — |
| 5'-28 | TAGGGTGCTTGCGAGTGCC | SEQ ID NO. 28 | — |
| 5'-29 | CGGGAGGTCTCGTAGACCG | SEQ ID NO. 29 | — |
| 5'-30 | GGTCTCGTACACCGTGCAT | SEQ ID NO. 30 | — |
| | | | |
| C-1 | AGATCGTTGGTGGAGTTTA | SEQ ID NO. 31 | — |
| C-2 | gTTGGGTAAGGTCATCGATA | SEQ ID NO. 32 | — |
| C-3 | GCCGACCTCATGGGGTACAT | SEQ ID NO. 33 | 18 |
| C-4 | GGTTGCTCTTTCTCTATCT | SEQ ID NO. 34 | — |
| C-5 | GGGATATGATGATGAACTG | SEQ ID NO. 35 | — |
| C-6 | GGATGAACCGGCTAATAGC | SEQ ID NO. 36 | — |
| C-7 | GGAGATGGGCGGCAACATC | SEQ ID NO. 37 | — |
| C-8 | GTCTTCACGGAGGCTATGA | SEQ ID NO. 38 | — |
| C-9 | GTCAACTCCTGGCTAGGCAA | SEQ ID NO. 39 | — |
| C-10 | gTCCACAGTTACTCTCCAGG | SEQ ID NO. 40 | — |
| C-11 | gCCTCTTCAACTGGGCAGTA | SEQ ID NO. 41 | — |
| C-12 | AGCTTAAACTCACTCCAAT | SEQ ID NO. 42 | C11&12, C6-C9-C12-3'1 |
| | | | |
| 3'-1 | GCTCCATCTTAGCCCTAGT | SEQ ID NO. 43 | 19 |
| 3'-2 | gTCCATCTTAGCCCTAGTCA | SEQ ID NO. 44 | 19 |
| 3'-3 | GTCACGGCTAGCTGTGAAA | SEQ ID NO. 45 | 19 |
| 3'-4 | ACGGCTAGCTGTGAAAGGT | SEQ ID NO. 46 | 19 |
| 3'-5 | GCTGTGAAAGGTCCGTGAG | SEQ ID NO. 47 | 19 |
| 3'-6 | GGTCCGTGAGCCGCATGAC | SEQ ID NO. 48 | — |
| 3'-7 | GCCGCATGACTGCAGAGAGT | SEQ ID NO. 49 | — |
| 3'-8 | ACTGGCCTCTCTGCAGATCA | SEQ ID NO. 50 | — |
| 3'-9 | TAGCCCTAGTCACGGCTAG | SEQ ID NO. 51 | — |
| 3'-10 | AGCTGTGAAAGGTCCGTGA | SEQ ID NO. 52 | — |
| 3'-11 | TAGCTGTGAAAGGTCCGTG | SEQ ID NO. 53 | — |
| 3'-12 | CTAGCTGTGAAAGGTCCGT | SEQ ID NO. 54 | — |
| 3'-13 | CTGTGAAAGGTCCGTGAGC | SEQ ID NO. 55 | — |
| 3'-14 | GAAAGGTCCGTGAGCCGCA | SEQ ID NO. 56 | — |

To test the efficacies of proposed RNAi agents, pre-synthesized RNAi agents were transfected into cells by standard techniques and reagents. An unrelated RNAi species was transfected into a parallel set of plates to serve as the negative control. Transfection efficiency was monitored by the co-transfection using a reporter plasmid expressing firefly luciferase. At various time points post-transfection, the level of target gene activity is measured by one of a variety of methods.

Example 2

Assessment of ApoE/Livpro RNAi Expression Constructs

Figure 6:
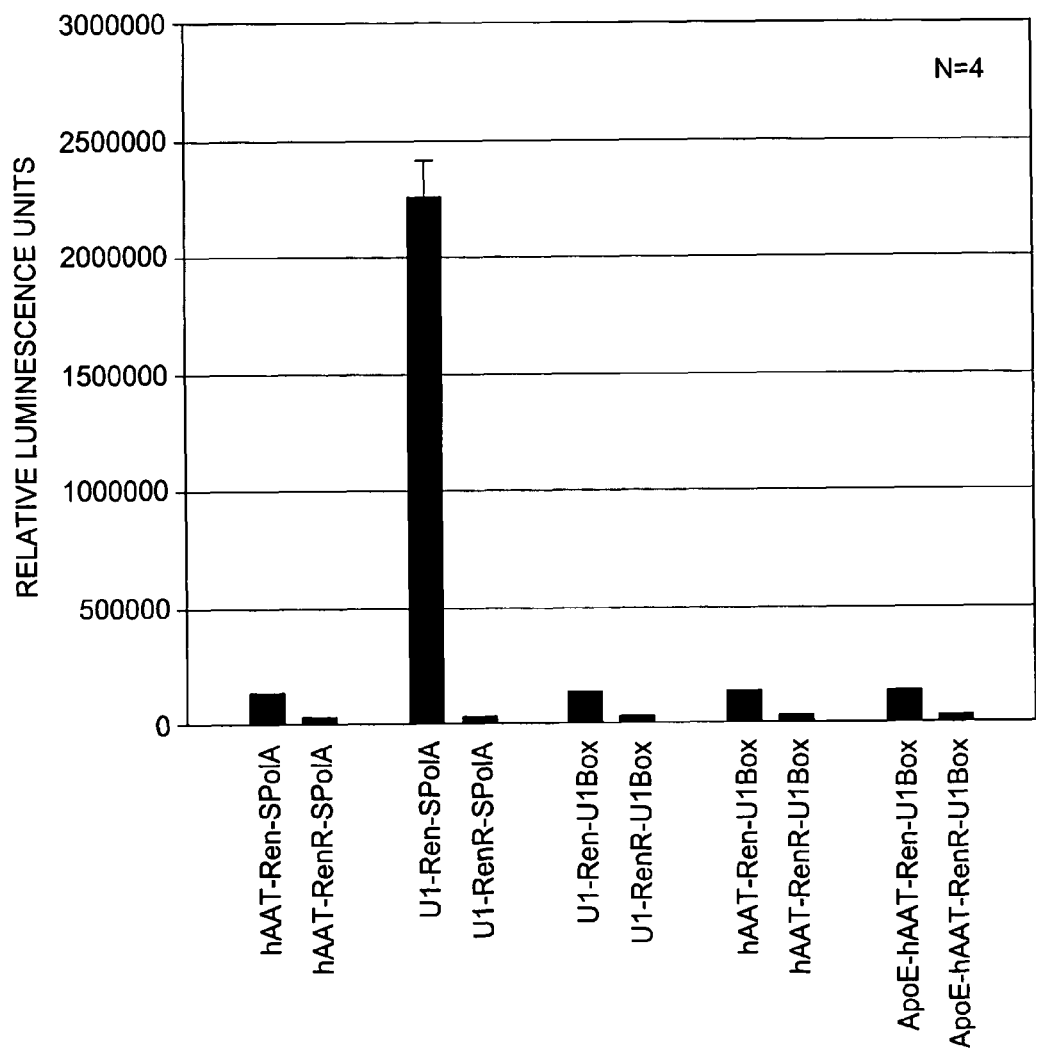
FIG. 6 shows data from an experiment comparing the relative activity of hAAT Pol II promoter and U1 Pol II promoter sequences, each driving the transcription of the *renilla* luciferase gene in either a correct or incorrect orientation. Additionally, the data shows the results of coupling these promoters with a synthetic poly A sequence or a U1 termination sequence.
Figure 7:
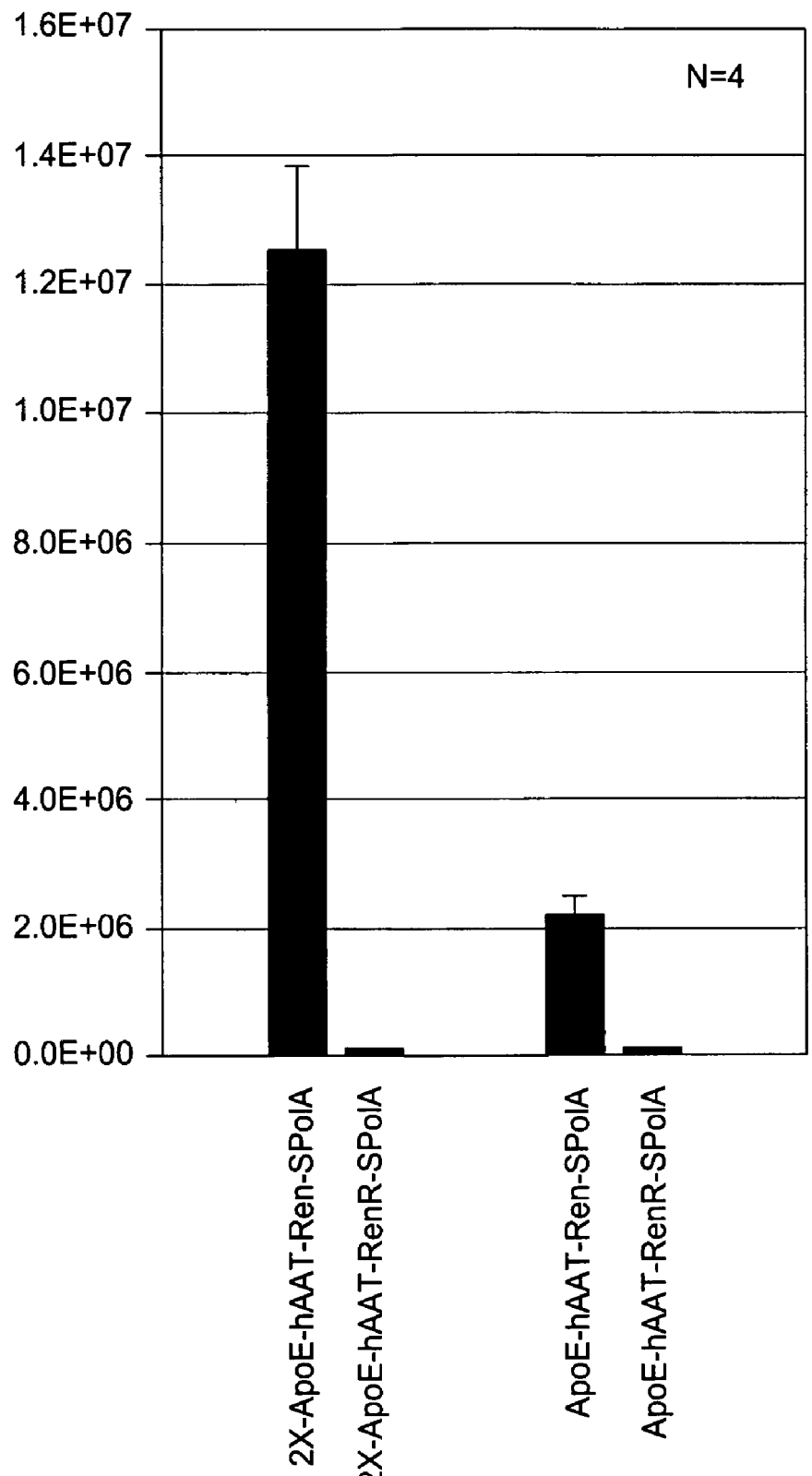
FIG. 7 shows data comparing activity of ApoE/livpro RNAi expression cassettes having either one or two (2×) ApoE enhancers in combination with a hAAT promoter driving a *renilla* luciferase gene in either a correct or incorrect orientation.
Figure 8:
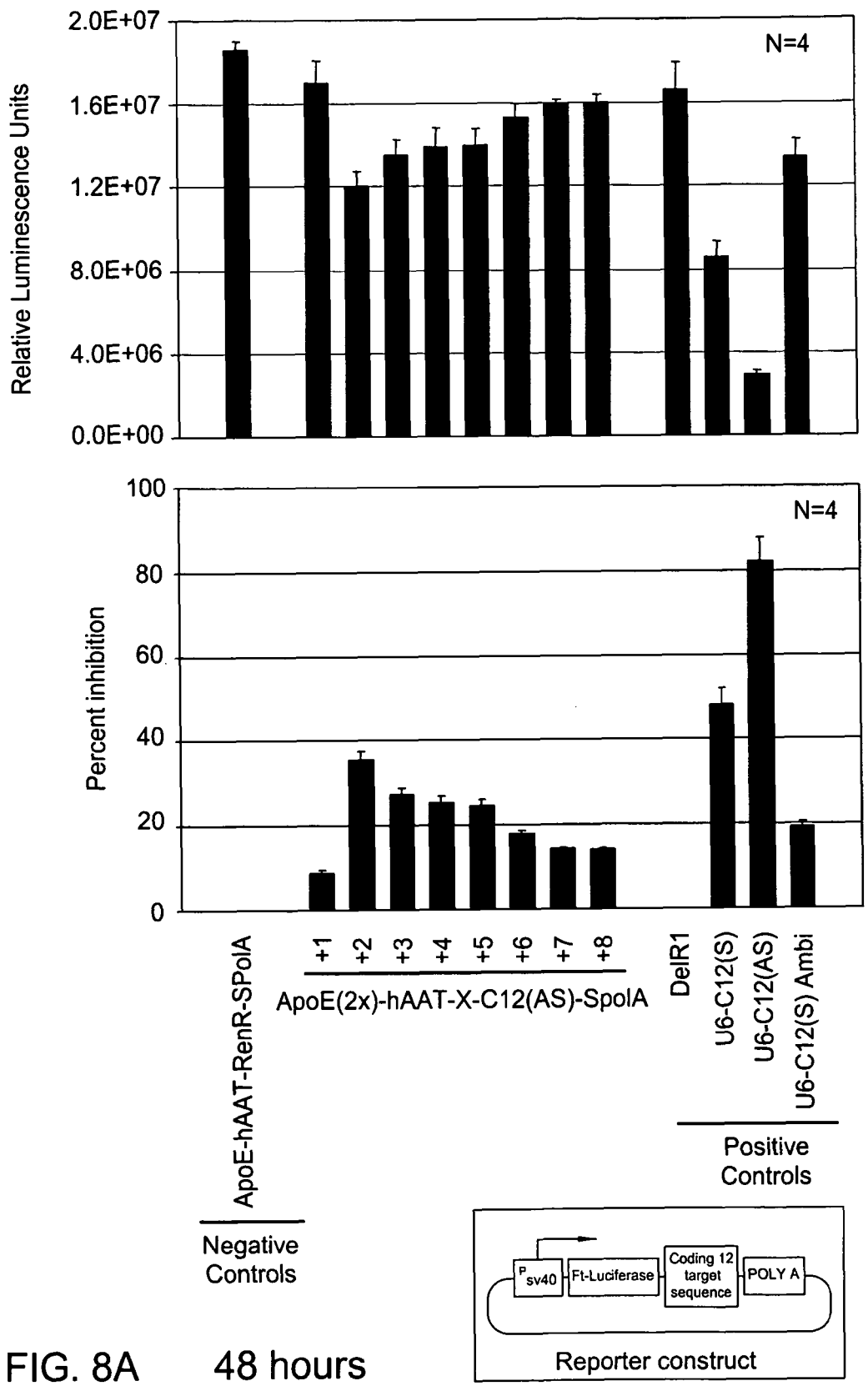
FIGS. 8A and 8B show data from two experiments where the activity of a luc-HCV sequence fusion reporter gene was measured while co-expressed with various 2×ApoE/hAAT/HCV shRNA expression constructs. One experiment measured activity at 48 hours post transfection (FIG. 8A), and the other experiment measured activity at 72 hours post transfection (FIG. 8B).

Utilization of liver-specific promoters such as the hAAT Pol II promoter to express RNAi agents is not a straightforward undertaking. Liver-specific promoters typically are Pol II promoters that produce transcripts where 5' cap structures and poly A sequences need to be added post-transcriptionally to protect the transcribed sequences from degradation from normal endogenous cellular nucleases. 5' cap structures are added to the 5' end of the transcribed sequence, and poly A structures are added in response to a recognition sequence, such as a U1 termination sequence (U1 box). However, RNAi agents with cap structures are not processed efficiently by the enzyme Drosha, rendering such RNAi agents ineffective. Thus, in order to use the hAAT promoter to drive the transcription of RNAi agents, several hurdles must be overcome, and for optimized transcription and processing of the RNAi agents, various parameters of the ApoE/livpro RNAi expression cassette components must be tested. Various experiments have been performed to allow for such optimization. Results for these experiments are shown in FIGS. 6-8 and are described below. In the experiments detailed in FIGS. 6 and 7, the individual promoter/enhancer and terminator components which make up the expression cassettes were tested in various combinations to ensure optimal expression levels in a liver-derived cell culture line. Each sample was co-transfected with two separate constructs: 1) a control or experimental ApoE/hAAT/Renilla expression construct, and 2) a construct expressing firefly luciferase (to allow for normalization of transfection efficiency).

In a one experiment, expression constructs utilizing either the hAAT promoter or the U1 basic promoter (both Pol II promoters) were tested. Four independent transfections were performed with each expression construct and the transfected cells were harvested 72 hours post-transfection and assayed for *renilla* luciferase activity. An expression plasmid for firefly luciferase was co-transfected with the experimental plasmid in each sample to normalize for transfection efficiency. The results of this experiment are shown in FIG. 6. The experimental plasmids included the hAAT promoter (designated hAAT), the U1 promoter (U1) or the ApoE/hAAT enhancer promoter combination (ApoE-hAAT). In order to assess the relative success of each combination, the experimental plasmids expressed the *Renilla luciferase* gene either in a correct orientation (Ren), or a reverse orientation (RenR) with the latter leading to the generation of a negative control for each experimental plasmid. The experimental plasmids also either included a synthetic poly A sequence (SpolA) or a U1 box (a termination sequence commonly associated with the U1 promoter sequence). The graph of the results obtained from the experiment shown in FIG. 6 indicate that there is modest activity from the plasmid driven by the U1 promoter and terminated with the synthetic poly A sequence (SpolA); however, little activity was measured using the other constructs.

FIG. 7 shows data comparing the activity of ApoE/livpro RNAi expression cassettes having either one (ApoE) or two (2×ApoE) ApoE enhancers, along with a hAAT promoter driving a *renilla* luciferase gene in either a correct (Ren) or incorrect (RenR) orientation. A synthetic poly A sequence (SpolA) was used in all constructs. Note that a significantly higher level of activity was obtained with the addition of a single ApoE enhancer element (note the differences in scale of the y axis); however, the presence of a second ApoE enhancer further increased the level of activity by nearly an order of magnitude.

In experiments detailed in FIGS. 8A and 8B, each sample was co-transfected with three separate constructs: 1) a control of experimental ApoE/hAAT/RNAi expression construct, 2) a luc-fusion reporter construct (bottom of FIG. 8A); and 3) a construct expressing *renilla* luciferase (to allow for normalization of transfection efficiency). Specifically, the Luc-fusion reporter plasmid was co-transfected into Huh-7 cells with experimental shRNA expression plasmids encoding hairpin RNAi sequences against the coding-12 (C12) target region of HCV. Each of the experimental shRNA expression plasmids contained the 2×ApoE enhancer element and the hAAT promoter, and varied only in the start position of the C12 sequence (i.e., the start position of the C12 sequence relative to the transcription initiation point varied between the experimental plasmids by 1, 2, 3, 4, 5, 6, 7, and 8 nucleotides). In some cases, a synthetic poly A sequence (SpolA) was, used, while in other cases, the U1 box was used. A total of four independent transfections were used for each condition. In one experiment (the results of which are shown in FIG. 8A), the samples were harvested at 48 hours post-transfection, and in another experiment (the results of which are shown in FIG. 8B), the samples were harvested at 72 hours post-transfection. Each sample was assayed for relative levels of firefly luciferase activity (normalized to *renilla* activity which controls for differences in transfection efficiency). The raw data is shown in the top graph. Data was normalized and the percent inhibition (lower panel) was calculated against various negative control expression constructs.

Note that at the addition of only one nucleotide before the start position of the C12 sequence relative to the transcription initiation point resulted in little activity. However, addition of two nucleotides before the start position of the C12 sequence relative to the transcription initiation point resulted in enhanced activity, where such activity was retained for constructs having three, four and five nucleotides before the start position of the C12 sequence relative to the transcription initiation point. However, the addition of nucleotides beyond five before the start position of the C12 sequence relative to the transcription initiation point resulted in a drop in activity. In addition, FIG. 8 also shows how the 2×ApoE/hAAT combination functions relative to the strong, constitutively-acitve U6 Pol III promoter (see the positive controls where the U6 promoter drives transcription of the HCV C12 sequence in both sense and antisense orientations). Note that though the 2×ApoE/hAAT constructs did not show comparable activity to the U6 Pol II promoter constructs at 48 hours; however, at 72 hours the activity was improved.

It should be noted that addition of nucleotides to the C12 sequence results in a relative and not absolute pattern of optimal activity. In our example the optimal number of nucleotides to be added is between 1 and 4. This number is however dependent on the exact position of the transcription initiation nucleotide of the hAAT promoter construct used. If in a construct this so-called +1 nucleotide lies further upstream of the shRNA, the number of extra nucleotides would relatively shift up, while if it lies further towards the shRNA, the number of nucleotides would relatively shift down.

Example 3

Assessment of ApoE/hAAT RNAi Expression Constructs

A pol II expression construct including a fusion promoter containing the human ApoE-hepatic control region (HCR) enhancer and the human alpha-1 antitrypsin promoter (ApoE/hAAT) was tested in transgenic mice. The human ApoE-hepatic control region (HCR) enhancer is an ApoE enhancer element as defined herein and is further described in Miao, et al., Molecular Therapy, June 2000: 1(6): 522-532, which is incorporated by reference herein. The pol II expression construct also included an RNAi construct that is under the control of the fusion promoter and that provides a hairpin (shRNA). The sequence of the fusion promoter is GTTTCTGGGCTCACCCTGCCCCCTTC- CAACCCCTCAGTTCCCATCCTCCAGCA GCTGTTTGTGTGCTGCCTCTGAAGTCCACACTGAACAAACTTCAGCCTACTCATGTCCCTAAAATGGGCAAACATTGCAAGCAGCAAACAGCAAACACACAGCCCTC CCTGCCTGCTGACCTTGGAGCTGGGGCAGAGGTCAGAGACCTCTCTGGGCCCATGCCACCTCCAACATCCACTCGACCCCTTGGAATTTCGGTGGAGAGGAGCAG AGGTTGTCCTGGCGTGGTTTAGGTAGTGTGAGAGGGGTACCCGGGGATCTTGCTACCAGTGGAACAGCCACTAAGGATTCTGCAGTGAGAGCAGAGGGCCAGCTA AGTGGTACTCTCCCAGAGACTGTCTGACTCACGCCACCCCCTCCACCTTGGACACAGGACGCTGTGGTTTCTGAGCCAGGTACAATGACTCCTTTCGGTAAGTGCA GTGGAAGCTGTACACTGCCCAGGCAAAGCGTCCGGGCAGCGTAGGCGGGCGACTCAGATCCCAGCCAGTGGACTTAGCCCCTGTTTGCTCCTCCGATAACTGGG GTGACCTTGGTTAATATTCACCAGCAGCCTCCCCCGTTGCCCCTCTGGATCCACTGCTTAAATACGGACGAGGACAGGGCCCT (SEQ ID NO:63), with the first 319 nucleotides being the ApoE-hepatic control region (HCR) enhancer, and the remainder of the nucleotides being a hAAT promoter. The hairpin used for these studies was 25 nucleotides in length (25mer). The DNA sequence of the RNAi construct for the hairpin is GAA-CAAATGGCACTAGTAAACTGAGtcaagagCTCAGTTTACTAGTGCCATTTGTT C (SEQ ID NO:64). The lower case 7 nucleotide stretch of the sequence provides the loop region of the hairpin. The hairpin targets the hepatitis B virus s-antigen (HBV sAg), and was previously demonstrated to have toxic effects when driven by the U6 promoter, which is a commonly used promoter. The toxic effects observed for the U6 construct was such that the ultimate result was either loss of the RNAi silencing effect or the death of recipient mice less than a month following delivery by injection of expression cassette-harboring adeno-associate virus (AAV).

The ApoE/hAAT-driven 25mer, terminated by a U1 snRNA 3'box, was packaged double-strand in pseudotyped AAV serotype-8 (dsAAV8). Transgenic mice received $1\times10^{11}$ or $3\times10^{11}$ viral particles via tail vein injection of the ApoE/hAAT-driven 25mer construct or a control ApoE/hAAT-driven anti-luciferase hairpin construct. The mice, initially three per group, were followed for approximately three months for changes in serum sAg, as determined by ELISA (FIGS. 10 and 11A-D). After four weeks, sAg levels in treated mice had decreased by an average of ~80%, and remained stable for the duration of the experiment. sAg levels in control mice decreased gradually over the course of the experiment, which is not atypical for this transgenic mouse line. However, the drop in these control mice was not as sudden or as great overall as for the mice that received the ApoE/hAAT-driven 25mer construct.

Figure 12:
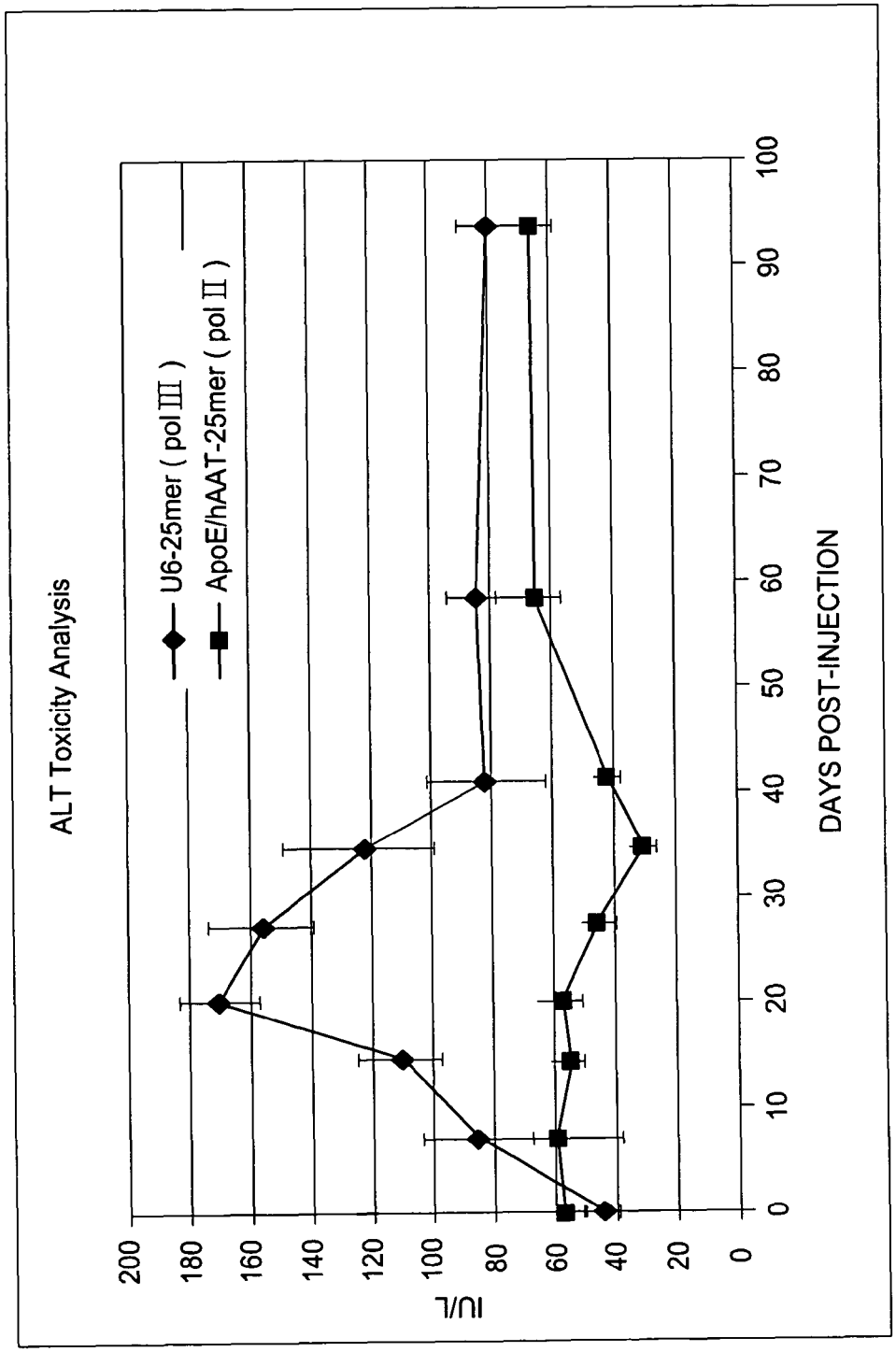
FIG. 12 shows the average serum alanine aminotransferase (ALT) concentrations in international units per liter (IU/L), as measured by a calorimetric assay, for healthy FVB mice that received dsAAV8-packaged expression cassettes for the expression of either U6- or ApoE/hAAT-driven 25mer hairpins against HBV sAg. All mice received doses of 3×10$^{11}$ viral particles, which was the high dose for the experiment illustrated in FIG. 10.

Healthy FVB mice were used in a toxicity study for direct comparison of U6- and ApoE/hAAT driven 25mers. Six mice per group received $3\times10^{11}$ of either of the dsAAV8-packaged constructs by tail vein injection. Serum ALT levels, a common measure of liver toxicity and damage, were followed over three months by colorimetric assay (FIG. 12). Three mice were sacrificed over the course of the experiment for liver collection, and error bars account for this (±1 standard deviation). Mice that received the ApoE/hAAT-driven construct had stable ALT levels, while mice that received the U6-driven construct had ALT levels that spiked to a peak around three weeks post-injection before returning to normal. This is consistent with the time frame over which sAg expression silencing is lost for the U6 construct on account of this toxicity.

Thus, the pol II expression construct provided herein that comprises an ApoE enhancer element (the ApoE-HCR) and a hAAT promoter driving the expression of a shRNA from an RNAi construct has been demonstrated to be an effective HBV therapeutic in a mouse model and has a safer toxicity profile than current systems for inducing RNAi, such as U6 systems.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material or process to the objective, spirit and scope of the present invention. All such modifications are intended to be within the scope of the invention.

All references cited herein are to aid in the understanding of the invention, and are incorporated in their entireties for all purposes without limitation.

What is claimed is:

1. A DNA directed RNA interference (ddRNAi) expression construct comprising:

- one or more enhancer elements selected from the group consisting of ApoE enhancer elements and SynEnh enhancer elements;
- one or more liver-specific promoters; and
- one or more RNAi constructs that provide three or more RNAi agents;
- wherein the RNAi agents target hepatitis virus genes that are desired to be repressed in a liver cell or whole liver, and wherein at least one of the three or more RNAi agents is coded by SEQ ID NO: 42.

2. The ddRNAi expression construct of claim 1, wherein the expression construct comprises one liver-specific promoter and the one or more RNAi constructs provide three RNAi agents.

3. The ddRNAi expression construct of claim 1, wherein each of the RNAi agents have different sequences.

4. The ddRNAi expression construct of claim 1, wherein the RNAi agents are expressed as shRNAs.

5. The ddRNAi expression construct of claim 4, further comprising nucleotides between a transcription initiation point of the expression construct and a first nucleotide of the one or more RNAi constructs.

6. The ddRNAi expression construct of claim 1, wherein the RNAi agent is part of a primary microRNA structure.

7. The ddRNAi expression construct of claim 1, further comprising a reporter gene.

8. The ddRNAi expression construct of claim 1, further comprising a terminator.

9. The ddRNAi expression construct of claim 8, further comprising a transcriptional pause site.

10. The ddRNAi expression construct of claim 1, wherein the other RNAi agents are coded by one or more of SEQ ID NO: 1-56.

11. The ddRNAi expression construct of claim 1, wherein the one or more promoters are selected from the group consisting of a hAAT promoter, an LCAT promoter, an ApoH promoter, and a transthyretin promoter.

12. A method of modifying the expression of one or more hepatitis virus genes in the liver, comprising delivering to the liver a DNA directed RNA interference (ddRNAi) expression construct comprising:

- one or more enhancer elements selected from the group consisting of ApoE enhancer elements and SynEnh enhancer elements;
- one or more liver-specific promoters; and
- one or more RNAi constructs that provide three or more RNAi agents,
- wherein at least one of the three or more RNAi agents is coded by SEQ ID NO: 42.

13. The ddRNAi expression construct of claim 12, wherein the RNAi agents are expressed as shRNAs.

14. The ddRNAi expression construct of claim 13, further comprising nucleotides between a transcription initiation point of the expression construct and a first nucleotide of the one or more RNAi constructs.

15. The ddRNAi expression construct of claim 12, wherein the other RNAi agents are coded by one or more of SEQ ID NO: 1-56.

16. The ddRNAi expression construct of claim 12, wherein the one or more promoters are selected from the group consisting of a hAAT promoter, an LCAT promoter, an ApoH promoter, and a transthyretin promoter.

* * * * *